US012806432B2

(12) United States Patent
Dapprich

(10) Patent No.: US 12,806,432 B2
(45) Date of Patent: Nov. 24, 2026

(54) METHOD AND COMPOSITIONS FOR CREATING MAGNETICALLY ALIGNED, BIOACTIVE SCAFFOLDS FOR TISSUE REGENERATION

(71) Applicant: Johannes Dapprich, Princeton, NJ (US)

(72) Inventor: Johannes Dapprich, Princeton, NJ (US)

( * ) Notice: Subject to any disclaimer, the term of this patent is extended or adjusted under 35 U.S.C. 154(b) by 942 days.

(21) Appl. No.: 18/098,690

(22) Filed: Jan. 18, 2023

(65) Prior Publication Data

US 2023/0347161 A1 Nov. 2, 2023

Related U.S. Application Data

(60) Provisional application No. 63/361,022, filed on Nov. 18, 2021.

(51) Int. Cl.
*A61N 2/00* (2006.01)
*C07K 7/06* (2006.01)
*C07K 7/08* (2006.01)

(52) U.S. Cl.
CPC ............. *A61N 2/006* (2013.01); *A61N 2/002* (2013.01); *C07K 7/06* (2013.01); *C07K 7/08* (2013.01)

(58) Field of Classification Search
CPC .......... A61N 2/006; A61N 2/002; C07K 7/06; C07K 7/08
See application file for complete search history.

(56) References Cited

U.S. PATENT DOCUMENTS

2011/0221438 A1* 9/2011 Goodwill ............. A61B 5/0515 324/301
2017/0021056 A1* 1/2017 Stupp ...................... A61L 27/18
2018/0064951 A1* 3/2018 Dapprich .............. A61L 27/446

OTHER PUBLICATIONS

Bannwarth et al., Colloidal Polymers with Controlled Sequence and Branching Constructed from Magnetic Field Assembled Nanoparticles, ACS Nano, vol. 9' No. 3' 2720-2728' 2015.*

* cited by examiner

*Primary Examiner* — Bo Joseph Peng
(74) *Attorney, Agent, or Firm* — MEAGHER EMANUEL LAKS GOLDBERG & LIAO, LLP

(57) ABSTRACT

Composition and method of regenerating a nerve fiber in a damaged neural tissue of a patient, the method includes: administering an aqueous formulation comprising magnetic particles to the damaged neural tissue in the patient; applying a magnetic field in an orientation which is parallel to the nerve fiber; using the magnetic field for aligning the magnetic particles; forming one or more aligned chains of the magnetic particles in the magnetic field as a scaffold to guide directional growth of regenerating nerve cells; and reconnecting damaged nerve ends in the damaged neural tissue of the patient.

18 Claims, 14 Drawing Sheets

Specification includes a Sequence Listing.

3001 3003 3004 3005

3006

METHOD AND COMPOSITIONS FOR CREATING MAGNETICALLY ALIGNED, BIOACTIVE SCAFFOLDS FOR TISSUE REGENERATION

CROSS-REFERENCE TO RELATED APPLICATIONS

The present US non provisional patent application claims the benefit of priority from a U.S. Provisional Patent Appl. No. 63/361,022 filed on Nov. 18, 2021, which is incorporated herein by reference in its entirety.

The Sequence Listing XML that is contained in the file named "dapprich.xml", which is 14899 bytes (as measured in Microsoft Windows®) and was created on Jul. 19, 2023, is filed herewith by electronic submission, and is incorporated by reference herein.

FIELD OF INVENTION

The present invention relates to a composition and method for tissue growth, and more particularly, the present invention relates to a composition and method for creating magnetically aligned bioactive scaffolds for neuronal tissue regeneration.

BACKGROUND

The regeneration of axonal connections after spinal cord injury is the subject of intense research. More than 17,000 new spinal cord injury cases are reported each year adding to the estimate 300,000 people currently living with spinal cord injury in the United States. Though neurites from spinal cord injury site stumps are able to grow as long as they are not inhibited by scar formation, it is widely recognized that developing a therapeutic technology that can facilitate directed axon regrowth within the 'golden hour' after injury would be a significant advance.

To this end, implantable and injectable tissue scaffolds, matrices and fibers are poised to be a major advancement and several have been demonstrated as safe in clinical trials. However, previous work has also shown that axonal regrowth can be oriented and even stimulated by specialized fibers. In addition, current scaffolds need to be customized to the shape of the injury site and then constructed and implanted, all under sterile conditions. Doing so requires additional time, specialized equipment that is often unavailable at most trauma centers and poses increased surgical risk to the cord. Moreover, specialized fibers do not address various contributing factors such as spinal cord motion, fibrinous clot formation, and the different viscosities of injured versus intact tissue and grey versus white matter. These limitations and others in existing technologies prevent the successful orientation of prefabricated fibers of sufficient length in situ.

The signaling of cells by scaffolds of synthetic molecules that mimic proteins has been known to be effective in the regeneration of tissues. Peptide amphiphile supramolecular polymers containing two distinct signals (peptide sequences) have been shown to activate the transmembrane receptor b1-integrin and a second one activates the basic fibroblast growth factor 2 receptor. Mutating the peptide sequence of the amphiphilic monomers in non-bioactive domains can intensify the motions of molecules within scaffold fibrils or fibers. This results in notable differences in vascular growth, axonal regeneration, myelination, survival of motor neurons, reduced gliosis, and functional recovery, indicating that the signaling of cells by ensembles of molecules can be optimized by tuning their internal motions.

The application of static or changing/modulated/oscillating magnetic fields has also been shown to affect cellular signaling, behavior and stimulated growth. Two examples that are approved for clinical use in humans are to speed up the healing of bone fractures and hyperthermia treatments to treat cancer. Surprisingly, the effects of an electromagnetically applied field can also extend to individual cells when they are exposed to magnetic nanoparticles typically used for hyperthermia applications even though under those conditions no significant elevation in temperature can be induced. However, such technologies have so far limited applications.

The successful regeneration of axonal connections after spinal cord injury (SCI) is an unsolved problem that prevents possible improvements in the lives of tens of thousands of patients with spinal cord injury. A therapeutic approach that can facilitate directed axon regrowth with potential functional reconnection after injury would be a significant advance. A need is therefore appreciated for a composition and method that overcomes the limitations with known formulations and therapies.

SUMMARY OF THE INVENTION

The following presents a simplified summary of one or more embodiments of the present invention to provide a basic understanding of such embodiments. This summary is not an extensive overview of all contemplated embodiments and is intended to neither identify critical elements of all embodiments nor delineate the scope of any or all embodiments. Its sole purpose is to present some concepts of one or more embodiments in a simplified form as a prelude to the more detailed description that is presented later.

In one aspect, disclosed are the compositions and method that combines the beneficial and growth-inducing effects of cellular activation, growth stimulation and directed growth through the effects of aligned fiber scaffolds or supporting hydrogel matrices that are functionalized with agents such as 'neuronal recovery activators' (NRAs). NRAs may comprise peptide amphiphile (PA) molecules, or peptide amphiphile supramolecular polymers. PAs preferably comprise the peptide sequences IKVAV or YRSRKYSSWYVALKR.

In one aspect, the disclosed composition and method have synergistic effects in tissue regrowth. The disclosed composition and method enhance the surprising benefits of cellular activation by NRAs by additionally providing an aligned scaffold. An aligned scaffold can comprise self-assembling fibers/fibrils and one or more NRAs. NRAs or PAs comprising NRAs can be attached or cross-linked to nanoparticles or fibers by functionalization of the nanoparticles or fibers through various types of binding and ligand/receptor combinations. The resulting complex is hereinafter called neuronal growth activating complex (NGAC). Nanoparticles or fibers can be magnetic or non-magnetic. Functionalization can optionally be performed before or after the formation or alignment of nanoparticles or fibers into a parallel scaffold in the injury site.

In one aspect, the disclosed method includes a step of functionalizing surfaces of the nanoparticles or fibers with one or the more chemical moieties prior administering an aqueous formulation having the nanoparticles or fibers to the damaged neural tissue in the patient, wherein the surfaces of the nanoparticles or fibers can be functionalized with the one or more chemical moieties including: carbohydrates, proteins, lipids, a glass, oligosaccharides, peptides, cross linking agents, thiols, sulfides, oxides, sulfhydryl, sulfides, disulfides, sulfinyl, sulfoxides, sulfonyl, a sulfones, sulfinic acid, sulfino, sulfonic acid, sulfo, thioketone, carbonothioyl, thial, primary amine, secondary amine, tertiary amine, carboxylate, carboxyl, alkoxy, hydroperoxy, peroxy, alkyl, alkene, alkyne, aryl derivative, oleic acid, synthetic opioid peptide, DAMGO ([D-Ala2, N-MePhe4, Gly-ol]-enkephalin, DAGO, DANGO, other drugs binding to a receptor structure H-Tyr-D-Ala-Gly-N-MePhe-Gly-ol, DPDPE ([d-Pen2,d-Pen5]enkephalin), tetrapeptide TAPS (Tyr-d-Arg-Phe-Sar), metkephamid, neuronal growth factor (NGF), anti-Nogo-A (i.e. inhibitor of Nogo-A 2), PEG, PEG linker, an antibody, a nucleic acid, a nucleic acid vector, RGD peptide, a therapeutic molecule, a fluorophore, a halo group, a hydroxyl, a carbonyl, an aldehyde, an acyl halide, an ester, a carbonate ester, an ether, a hemi acetal, a hemiketal, a ketal, an orthoester, a methyledioxy, a cycloalkyl, a heterocyclic, a heteroaryl, an orthocarbonate ester, a carboxamide, a primary ketimine, a secondary ketamine, a primary aldimine, a secondary aldimine, an imide, a nitro, a phosphonic acid, a phosphate, a phosphodiester, a nitrile, an isonitrile, an isocyanate, a an antibody, a pharmaceutical excipient, a pH buffer, a cerium oxide nanoparticles, a manganese dioxide nanoparticle, EDTA, EGTA, NTA, HEDTA, a cytokine, a cell, a liposome, a ligand that improves the passage of a pharmaceutical agent across the blood brain barrier or the blood-cerebrospinal fluid (CSF) barrier, a drug for specific biomedical applications, a PEG linker comprising any of the moieties listed above, and includes combination thereof.

In other preferred embodiments, the method further comprises prior functionalizing the surfaces of the nanoparticles or fibers with the one or more chemical moieties to promote chemical bonding between the nanoparticles or fibers and the Pas while the nanoparticles or fibers being aligned under a magnetic field and forming the one or more aligned chains of the nanoparticles or fibers parallel to the nerve fiber.

In some invention method embodiments, an aqueous formulation comprising the nanoparticles or fibers further comprises a molecule selected from the group consisting of a neuronal cell growth factor, a chemotactic factor, a cell proliferation factor, a directional cell growth factor, a neuronal regeneration signaling molecule, a laminin, an inhibitor of glial cell induced scar formation, an inhibitor of astrocyte cell induced scar formation, an inhibitor of oligodendrocyte cell induced scar formation, an inhibitor of astrocyte precursor cell induced scar formation, an inhibitor of oligodendrocyte precursor cell induced scar formation, an inhibitor of 4 sulfation on astrocyte derived chondroitin sulfate proteoglycan, an inhibitor of chondroitin sulfate proteoglycan phosphacan, an inhibitor of chondroitin sulfate proteoglycan neurocan, a chondroitinase ABC, an inhibitor of chondroitin sulfate proteoglycan 4, an inhibitor of neuron glial antigen 2, an antibody to chondroitin sulfate proteoglycan 4, an antibody against neuron glial antigen 2, an inhibitor of glial cell expression of chondroitin sulfate proteoglycan 4, an inhibitor of glial cell expression of neuron glial antigen 2, an inhibitor of keratan sulfate synthesis, an inhibitor of glial cell expression of an enzyme involved in keratin sulfate synthesis, an inhibitor of an oligodendritic cell debris origin neuroregeneration inhibiting protein, an inhibitor of a glial cell debris origin neuroregeneration inhibiting protein, an antibody against myelination inhibitory factor NI 35, an antibody against myelination inhibitory factor NOGO, anti-oxidants, cerium oxide nanoparticles, an amino acid, a phospholipid, a lipid, a vitamin, an anticoagulant, and a combination thereof.

In one aspect, the aqueous formulation comprising the nanoparticles or fibers further optionally comprises a carrier which is microspheres, porous particles, a gel, a hydrogel, a multiphase solution, a colloid, a capsule, a microcapsule, a liposome, an isotonic saline, a cerebrospinal fluid, or a combination thereof.

In one aspect, the method further comprises the step of stabilizing the aligned chains of the nanoparticles or fibers in the magnetic field using a cross linking polymer architecture for locking the aligned chains of the nanoparticles or fibers into place after using a magnetic field for aligning the nanoparticles or fibers and forming one or more aligned chains or structures of the nanoparticles or fibers in the magnetic field as the scaffold to guide directional growth of regenerating nerve cells.

In one aspect, the method further comprises the step of stabilizing the aligned chains of the nanoparticles or fibers in the magnetic field using a crosslinking polymer architecture for locking the aligned chains of the nanoparticles or fibers into place after the step of using the magnetic field for aligning the nanoparticles or fibers in the orientation which is parallel to the nerve fiber orientation in the damaged neural tissue and forming the one or more aligned chains of the nanoparticles or fibers in the magnetic field in the orientation which is parallel to the nerve fiber orientation in the damaged neural tissue, and before the step of using the one or more aligned chains of the nanoparticles or fibers in the orientation which is parallel to the nerve fiber orientation in the damaged neural tissue as a scaffold for regenerating the nerve fiber in the damaged neural tissue of the patient. In some invention method embodiments, the aligned chains of the nanoparticles or fibers that are the scaffold for regenerating the nerve fiber in the damaged neural tissue of the patient are stabilized by a cross linking polymer architecture In one aspect, the cross linking polymer architecture for forming or stabilizing NGACs or aligned chains of the nanoparticles or fibers is selected from the group consisting of a cross linking homopolymer of the surface functionalized superparamagnetic particles, a cross linking copolymer of different surface functionalized superparamagnetic particles, a cross linking junction controlled branched polymer of the surface functionalized superparamagnetic particles, and a combination thereof.

In one aspect, the cross linking polymer architecture for forming or stabilizing NGACs or the aligned chains of the nanoparticles or fibers is formed using molecules selected from the group consisting of psoralen, methyl methacrylate, avidin, streptavidin, antibodies, antigens, ligands, biotin, laminin, fluorescein, DNA hybridization molecules, DNA origami, DNA dendrimers, aptamers, protein protein binding, protein DNA binding, metal ion chelators, His tags, polyethylene glycol linkers, agarose, acrylamide, collagen, phase transfer catalysts, and any combination thereof.

In one aspect, the method further comprises the step of removing the magnetic field which is parallel to the nerve fiber orientation after the step of forming or stabilizing NGACs or the aligned chains of the nanoparticles or fibers using the cross-linking polymer architecture.

In one aspect, the nanoparticles or fibers have dimensions selected from the group consisting of between about 10-20 nm in diameter, between about 20 nm to 50 nm in diameter, between about 50 nm to 100 nm in diameter, between 100 nm to about 1 microns, between about 1 micron to about 20 microns in diameter, between about 2 microns to about 40 microns in diameter, between about 3 microns to about 10 microns in diameter, between about 1 micron to about 15 microns in diameter, between about 0.05 microns to about 100 microns in diameter, between about 5 microns to about 500 microns in diameter, and a combination thereof.

In some invention method embodiments, a magnetic field used to align the magnetic nanoparticles or the magnetic fibers has a strength between about 0.1 Gauss to 1 Gauss, between about 1 Gauss to 5 Gauss, between about 5 Gauss to 10 Gauss, between about 10 Gauss to 20 Gauss, between about 20 Gauss to 50 Gauss, between about 5 milli Tesla to about 50 milli Tesla, between about 50 milli Tesla to about 100 milli Tesla, between about 100 milli Tesla to about 500 milli Tesla, between about 0.5 Tesla to about 2 Tesla, between about 2 Tesla to about 10 Tesla.

In one aspect, magnetic fibers (either pre-existing fibers or fibers magnetically formed from chains of nanoparticles) are moved laterally towards severed nerve endings through the use of a magnetic field gradient. The magnetic field gradient can be applied after or during the formation of aligned fibers from chains of magnetic nanoparticles. A magnetic field gradient may be between 0.1 Gauss/m to 1 Gauss/m, between about 1 Gauss/m to 5 Gauss/m, between about 5 Gauss/m to 10 Gauss/m, between about 10 Gauss/m to 20 Gauss/m, between about 20 Gauss/m to 50 Gauss/m, between about 5 milli Tesla/m to about 50 milli Tesla/m, between about 50 milli Tesla/m to about 100 milli Tesla/m, between about 100 milli Tesla/m to about 500 milli Tesla/m, between about 0.5 Tesla/m to about 2 Tesla/m.

In one aspect, the damaged neural tissue is in the spinal cord of the patient. In some invention method embodiments, the damaged neural tissue of the patient is in the peripheral nervous system of the patient. In some invention method embodiments, the damaged neural tissue of the patient is in the optic nerve of the patient.

In one aspect, the cross-linking polymer architecture for stabilizing the aligned chains of the nanoparticles or fibers is formed using molecules selected from the group consisting of avidin, streptavidin, neutravidin, biotin, laminin, biotinylated DNA, DNA hybridization molecules, and any combination thereof.

In one aspect, the general invention method further comprises an earlier step of implanting the neural tissue from the patient into an area of the damaged neural tissue of the patient prior to the step of administering the aqueous formulation comprising the nanoparticles or fibers to the damaged neural tissue area in the patient.

In one aspect, disclosed are the methods wherein the earlier step of functionalizing the surfaces of the nanoparticles or fibers with one or more chemical moieties is for forming neuronal growth activating complexes (NGACs). The functionalized nanoparticles or fibers comprise more than one functionalization. For example, such functionalization may include several different neuronal recovery activators (NRAs), such as comprising the peptide sequences IKVAV (FIG. 1, FIG. 3-F5-1) or YRSRKYSSWYVALKR (FIG. 2, FIG. 3-F5-2). NRAs may comprise ligands for binding, attaching, stabilizing, or crosslinking them to nanoparticles or fibers from the groups listed above (FIG. 3, depicted as a star, 3011). The NRAs depicted in FIG. 3 as F5 can comprise either F5-1 or F5-2 or a combination thereof. The ligands depicted in FIG. 3, F1 can comprise any ligand or binding partner of a cognate binding pair as described above, or a combination thereof. A preferred combination is biotin and streptavidin. The invention embodiments include methods wherein the earlier step of functionalizing the surfaces of the nanoparticles or fibers with the one or more chemical moieties for forming the NGACs and NRAs is conducted in the presence of a magnetic field. Another preferred combination is a first chemical moiety as a thiol and a second chemical moiety as a primary amine. Another preferred combination is a first chemical moiety as a carboxylic acid and a second chemical moiety as a primary amine.

The addition of aligned and optionally magnetically generated fibers to the unexpectedly successful approach of enhancing the intensity of molecular motions with bioactive fibrils (peptide amphiphile supramolecular polymers, NRAs) creates a new type of biophysical environment that provides directionality to axonal regeneration, enhances neuronal growth and survival, and blood vessel regeneration through a novel combination of physical and cellular signaling stimuli, resulting in probable improved and accelerated functional recovery from SCI.

Examples for aligned fibers that may comprise NRAs and can be used as NGACs are: Biocompatible or biodegradable magnetic nanoparticles that are aligned into flexible fibers, termed 'fiberguides', through an externally applied magnetic field parallel to the intended direction of regrowth (fiberguides are described in U.S. Pat. No. 11,083,907 which is incorporated herein by reference to it in its entirety).

Fibers or the constituting nanoparticles can be functionalized with numerous different ligands, peptides, chemicals, biomolecules, coatings, structures, materials and any of the moieties and ligands listed above and combinations thereof.

Aligned magnetic fibers provide internal directional guidance to neurites within a three-dimensional collagen or fibrin model hydrogel, supplemented with Matrigel. Neurites growing from dorsal root ganglion explants extend about 2×-3× further on aligned fibers compared with neurites extending in a hydrogel alone.

Combined approaches as described in this invention are of interest for minimally invasive treatments for spinal cord repair, as well as for peripheral nerve repair and applications in the brain or other central nervous parts. Fibers can be injected and then magnetically positioned in situ, and the aligned fiber scaffolds provide consistent topographical guidance to cells. Neuron viability is enhanced both in two-dimensional and injectable three-dimensional scaffolds. Small conduits of aligned magnetic fibers are easily injected or formed in situ by a magnetic field in a collagen or fibrinogen hydrogel solution and can be repositioned using an external magnetic field.

The ultimate product will be a fast therapeutic treatment for SCI, consisting of an injectable gel formulation, a device to generate a temporary magnetic field in the injury site, and a protocol for use:

The Fibermag formulation will consist of two 'just-in-time' components (nanoparticles and crosslinker/matrix) which can be combined immediately before use. Mixing can be vortex mixing or can be done by using a small mixing nozzle with a Luer lock connector to attach an injection needle.

The formulation is injected into the injury site of an SCI patient and an external magnetic field can then be applied. Within minutes of magnetic field application, the magnetic nanoparticles align into parallel fiberguides/scaffolds, which automatically conform to any irregular volume of the injury and align with individual nerve endings, inducing/guiding them to grow along the intended path. The fiberguides are stable over weeks without magnetic field. The surrounding matrix helps to block scar formation and can be infused with agents that support regeneration.

For chronic injury treatment, debridement of the existing scar may first be performed.

The magnetic nanoparticle-infused hydrogel, the protocol, and the magnetic field design are all potential products resulting from this proposal.

Fibermag can provide several advantages over other existing and proposed scaffold-based treatments: in situ formation after injection that matches the shape of the injury site, comparatively simple and fast to administer, fiberguides remain flexible and are expected to both direct and stimulate axonal regeneration, and seamless pairing with other successful therapies.

Currently there are no real treatment options for SCI, whether acute or chronic. SCI includes very different types of injury patterns that typically require different surgical approaches for damage control, stabilization, and possible treatment. The major challenge in achieving complete functional recovery is to develop approaches that encourage directional axonal regeneration that extends through the lesion cavity and reconnects the two severed ends of the spinal cord. Axonal regeneration typically fails because of the formation of inhibitory fibrotic glial scar tissue at the lesion cavity within weeks after the injury, as well as due to the lack of directional guidance cues for axonal regrowth. A fibrotic scar forms within about two weeks of the injury and leads to a cascade of secondary injury that expands and exacerbates the original lesion through ischemia, elevated calcium levels, radical formation and inflammation that lead to astrogliosis. The scar impedes the regrowth of neurons rather than supporting neural cells, oligodendrocytes die, and the formation of new nerve cells is stopped. It is therefore of critical importance to quickly fill in the injury site with a suitable, biocompatible matrix, such as a hydrogel, in order to stop scar tissue from forming. However, this treatment alone does not promote axonal regeneration.

The disclosed biosimilar scaffold mimics the properties of native spinal cord tissue, which can likely enhance the effectiveness of other orthogonal approaches. The disclosed composition and method can generate a 3D scaffold in a matrix with oriented conduits that can guide the neurite growth along the intended path in order to successfully reach and connect the two respective ends of the severed cord.

Scaffolds for the possible treatment of spinal cord injury have been functionalized with surface groups, coatings, chemical moieties or other types of molecules that support or stimulate desired processes such as cellular adhesion to the scaffold, stimulation of regrowth, directionally aligned growth, axonal regeneration, functional reconnection and electrical conductivity. Such molecules can be used either on their own or in combination.

Examples include so-called 'biologically active' molecules, often peptides, that perform desirable physiological signaling functions that support a desired regeneration or other biological effect, or molecules that may suppress certain signaling functions of the living body that may otherwise have a detrimental biological effect. Specific examples of such signaling molecules used in the context of spinal cord regeneration are neuronal regrowth-enhancing molecules, such as the peptide YRSRKYSSWYVALKR that can promote cell proliferation and survival, the peptide IKVAV that can promote differentiation of neural stem cells into neurons and extend axons, (Alvarez et, or molecules that inhibit Nogo-A (or related biological signal/receptor mechanisms) that normally suppress neuronal growth in adult tissue and therefore block desirable regeneration after injury.

BRIEF DESCRIPTION OF THE DRAWINGS

The accompanying figures, which are incorporated herein, form part of the specification and illustrate embodiments of the present invention. Together with the description, the figures further explain the principles of the present invention and enable a person skilled in the relevant arts to make and use the invention.

DETAILED DESCRIPTION

Figure 1:
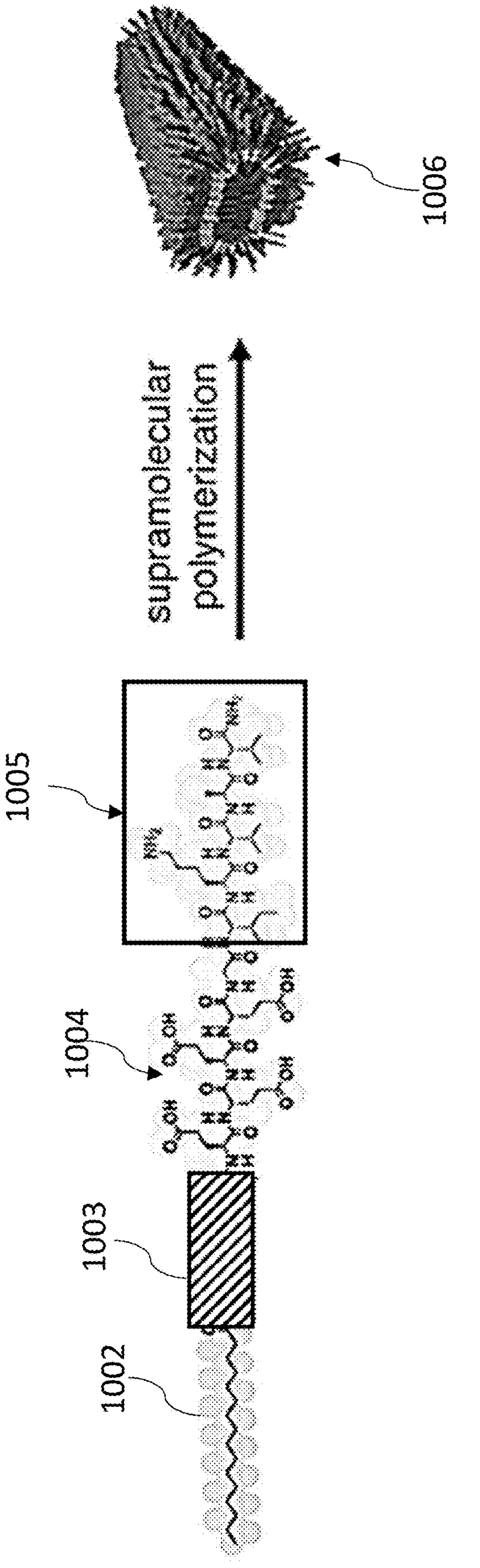
FIG. 1 shows an example of a peptide amphiphile (PA) subunit molecule and a peptide amphiphile supramolecular polymer, according to an exemplary embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, a reasonably broad scope for claimed or covered subject matter is intended. Among other things, for example, the subject matter may be embodied as apparatus and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is to describe particular embodiments only and is not intended to be limiting to embodiments of the invention. As used herein, the singular forms "a", "an" and "the" are intended to include the plural forms as well, unless the context indicates otherwise. It will be further understood that the terms "comprise", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth in order to provide a thorough understanding of the subject innovation. It may be evident, however, that the claimed subject matter may be practiced without these specific details. In other instances, well-known structures and apparatus are shown in block diagram form in order to facilitate describing the subject innovation. Moreover, the drawings may not be to scale.

Disclosed are a composition and method for promoting/enhancing/aiding/triggering tissue regeneration at an injured tissue site, such as regeneration of nerve fibers in a damaged neural tissue. The disclosed composition and method synergistically promote tissue growth by providing a scaffold for guiding the growth of nerve fibers along an intended path and promoting the tissue growth using bioactive molecules, such as neuronal regrowth-enhancing agents.

The disclosed composition can also include crosslinking agents, such as biocompatible hydrogel matrix. The ingredients of the composition including biocompatible magnetic nanoparticles, biologically active molecules NRAs, and others can be combined just before or during the administration of the composition. The composition can be formulated in an injectable form using several excipients. Use of such excipients for use in parental preparations are known to a skilled person.

The composition can chiefly contain three components, one component consists primarily of magnetic nanoparticles, a second component containing hydrogel-forming or cross-linking agents that stabilize the fibers of the scaffold after they have formed, and a third component that contains desired biologically active molecules. Two or more components are combined, typically shortly before injection into the injury site, to initiate surface functionalization of the fibers that are magnetically formed from the magnetic nanoparticles, and optional cross-linking of the magnetic nanoparticles.

Once injected, the fibers form through alignment by an externally applied magnetic field, and could be functionalized with the added bioactive molecules, once formed, the functionalized fibers can be stabilized, and the magnetic field can be removed. The resulting functionalized fiber scaffold automatically conforms to any irregular shape of the injury site. The functionalized individual fibers interdigitate with neuronal ends on both sides of the injury site, facilitating their attachment.

This invention relates to a minimally invasive method of treatment for SCI that comprises creating a bioactive combination of aligned fibers and neurotrophic microenvironment in situ at the injury site in the body of a patient for helping specific cells such as axons, neurites and nerve cells grow and regenerate in a preferred direction.

The invention preferably uses a combination of externally applied magnetic fields and a bioactive formulation that contains magnetic particles in a neurotrophic microenvironment, where the magnetic particles are aligned by the magnetic field to form a fibrous scaffold from the injected material that stimulates and guides regrowth of nerve cells in a desired direction. The bioactive formulation may comprise neurotrophic factors that may be attached with linkers to the magnetic particles, to the fibers, to the fibrous scaffold, to structures present in the microenvironment, and a combination thereof. Magnetic nanoparticles are also called magnetic particles.

The particles can be magnetic, ferromagnetic or superparamagnetic nanoparticles or microparticles, with typical dimensions being 10 to 50 nanometers, 50 to 200 nanometers, 100 to 200 nanometers, 200 to 500 nanometers, 500 to 750 nanometers, 750 nanometers to 1 micrometer, 1 to 2 micrometers, or larger in size. The particles can be spherical or non spherical and may or may not contain remnant magnetic moments when no external magnetic field is present. Elongated particles, nanorods or linked chains of particles are also desirable for this invention. Equally of interest are particles that form hollow or honeycomb like structures when or after they are subjected to a magnetic field, such as particles that are linked by certain linkers known in the art, or particles that are embedded in other matrices that are orientable by an externally applied magnetic field.

The magnetic particles, fibers and fibrous scaffolds may optionally be functionalized with bioactive molecules either before, during or after they have formed fibers, and either before, during or after they have been aligned and oriented into a scaffold. The desired type of bioactive scaffold in the application for spinal cord or other nerve reconstruction is that of a longitudinally oriented, parallel scaffold that allows for the growth of the nerve cells into one orientation and discourages growth directions that are not parallel to the alignment of the scaffolding.

In order to initiate and enhance nerve growth into a direction, neurotrophic factors, nerve growth factors, or particles or slow release vesicles containing such neurotrophic factors or nerve growth factors, can be injected and placed at specific positions in the scaffold so as to release growth factors and molecules that trigger a directed growth of the nerve cells is known in the art. For instance if two ends of the spinal cord are disconnected and the magnetic particles, fibers or fibrous scaffolds have been injected into the cavity, neurotrophic factors or nerve growth factors or other compounds that guide the direction of growth of the nerve cells can be locally injected at the center of the inserted formulation so as to create an incentive for the spinal cord nerve cells at each end of the injury site to grow towards the center where they may reconnect and re-establish an electrically functional nerve connection.

The injectable formulation may optionally also comprise embedded cells, stem cells, neural progenitor cells, induced pluripotent stem cells, induced pluripotent stem cell-derived neurons and other components that aid in the regeneration of directional axonal growth. Layer by layer building of such matrix/cell structures can form defined tissue constructs. Deposition of such layered structures may be done outside of the patient's body before injection or in situ at the injury site. Embedding specific types of cells in aligned scaffolds allows additional control of cell migration, interconnection and matrix remodeling in isotropic and anisotropic applications.

SUMMARY OF THE INVENTION

The invention generally relates to a method of regenerating a nerve fiber in a damaged neural tissue of a patient, the method comprising the steps of: administering an aqueous formulation comprising magnetic particles, bioactive molecules and a neurotrophic microenvironment to the damaged neural tissue in the patient; applying a magnetic field in an orientation which is parallel to the nerve fiber; using the magnetic field for aligning the magnetic particles; forming one or more aligned chains of the magnetic particles in the magnetic field as a scaffold to guide directional growth of regenerating nerve cells; and reconnecting damaged nerve ends in the damaged neural tissue of the patient.

In some invention method embodiments, the aqueous formulation comprising magnetic particles, bioactive molecules and a neurotrophic microenvironment further comprises a molecule selected from the group consisting of a neurotrophic factor, a neurotrophic factor peptide sequence, a neuronal cell growth factor, a chemotactic factor, a cell proliferation factor, a directional cell growth factor, a neuronal regeneration signaling molecule, a laminin, an inhibitor of glial cell induced scar formation, an inhibitor of astrocyte cell induced scar formation, an inhibitor of oligodendrocyte cell induced scar formation, an inhibitor of astrocyte precursor cell induced scar formation, an inhibitor of oligodendrocyte precursor cell induced scar formation, an inhibitor of 4 sulfation on astrocyte derived chondroitin sulfate proteoglycan, an inhibitor of chondroitin sulfate proteoglycan phosphacan, an inhibitor of chondroitin sulfate proteoglycan neurocan, a chondroitinase ABC, an inhibitor of chondroitin sulfate proteoglycan 4, an inhibitor of neuron glial antigen 2, an antibody to chondroitin sulfate proteoglycan 4, an antibody against neuron glial antigen 2, an inhibitor of glial cell expression of chondroitin sulfate proteoglycan 4, an inhibitor of glial cell expression of neuron glial antigen 2, an inhibitor of keratan sulfate synthesis, an inhibitor of glial cell expression of an enzyme involved in keratin sulfate synthesis, an inhibitor of an oligodendritic cell debris origin neuroregeneration inhibiting protein, an inhibitor of a glial cell debris origin neuroregeneration inhibiting protein, an antibody against myelination inhibitory factor NI 35, an antibody against myelination inhibitory factor NOGO, an anti-oxidants, cerium oxide nanoparticles, an amino acid, a phospholipid, a lipid, a vitamin, an anticoagulant, and a combination thereof.

In other preferred embodiments, the general invention method further comprises the step of stabilizing the aligned chains of the magnetic particles in the magnetic field using a crosslinking polymer architecture for locking the aligned chains of the magnetic particles into place as a scaffold to guide directional growth of regenerating nerve cells.

In some invention method embodiments, the damaged neural tissue of the patient is in the spinal cord of the patient. In some invention method embodiments, the damaged neural tissue of the patient is in the peripheral nervous system of the patient. In some invention method embodiments, the damaged neural tissue of the patient is in the optic nerve of the patient.

FIG. 1 depicts an example of a peptide amphiphile (PA) subunit. In this example, the PA subunit comprises an optional alkyl chain [1002], an optional flexible peptide linker sequence [1003], an optional linker peptide sequence [1004], and a neurotrophic factor peptide sequence [1005]. Multiple peptide amphiphile (PA) subunit can form a peptide amphiphile supramolecular polymer fibril complex [1006], also called fibrils or fibers. The neurotrophic factor peptide sequence [1005] can comprise different types of peptide sequences, each of which is intended to function as a bioactive molecule or neurotrophic factor, including when peptide amphiphile subunits comprising multiple NRAs are assembled into a larger complex such as [1006] and consisting of multiple peptide amphiphile subunits. Peptide amphiphile subunits in a peptide amphiphile supramolecular polymer fibril complex may be identical to each other or comprise diverse types of peptide amphiphile subunits. A peptide amphiphile supramolecular polymer may form fibrils such as [1006], fibers, vesicles, sheets or other structures, including through self-assembly. The neurotrophic factor peptide sequence [1005] in this example comprises the sequence IKVAV and is also known as a laminin signal peptide.

Figure 2:
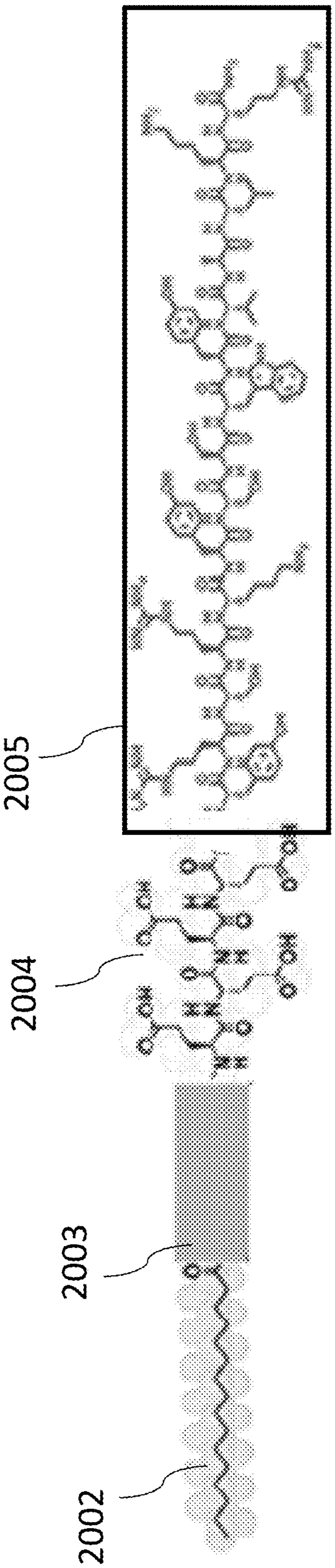
FIG. 2 shows another example of a peptide amphiphile (PA) subunit molecule.

FIG. 2 depicts an example of peptide amphiphile subunit capable of self-assembling into fibrils or fibers. In this example, the PA comprises an optional alkyl chain [2002], an optional flexible peptide linker sequence [2003], an optional linker peptide sequence [2004], and the neurotrophic factor peptide sequence [2005]. The neurotrophic factor peptide sequence [2005] in this example comprises the sequence YRSRKYSSWYVALKR and is also known as a fibroblast growth factor2 (FGF-2) mimetic signal peptide.

Figure 3:
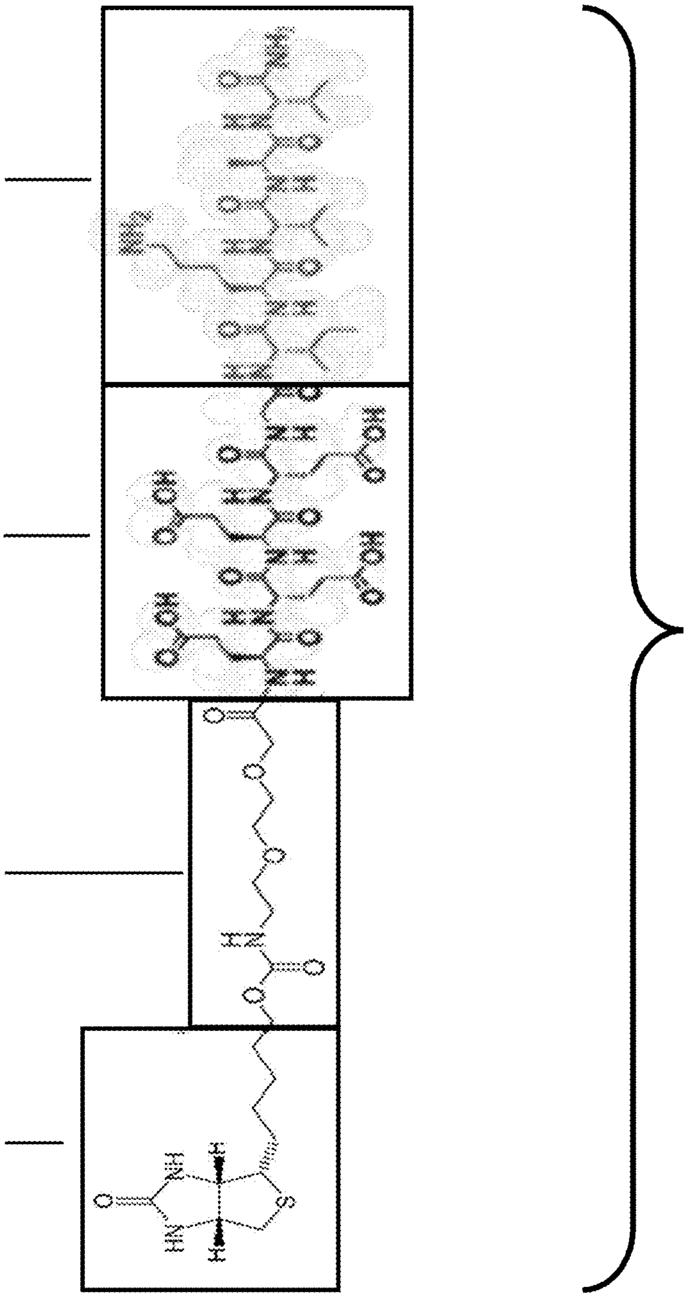
FIG. 3 is a schematic depiction of a neuronal recovery activator (NRA).

FIG. 3 depicts an example of a neuronal recovery activator (NRA) [3006] comprising a linker [3001] to a cognate ligand, an optional linker sequence [3003], an optional linker peptide sequence [3004], and a neurotrophic factor peptide sequence [3005] that functions as a neurotrophic factor or bioactive molecule. In this example, the linker [3001] is biotin, the designated cognate ligand (not depicted) is streptavidin or neutravidin, the linker sequence [3003] is a mini-polyethylene glycol (PEG), the linker peptide sequence [3004] is EEEEG, and the neurotrophic factor peptide sequence [3005] is IKVAV, also known as laminin signal peptide. An NRA may comprise one or more peptide amphiphile supramolecular polymer subunits and may be capable of self-assembling into fibrils or other types of structures.

Figure 4:
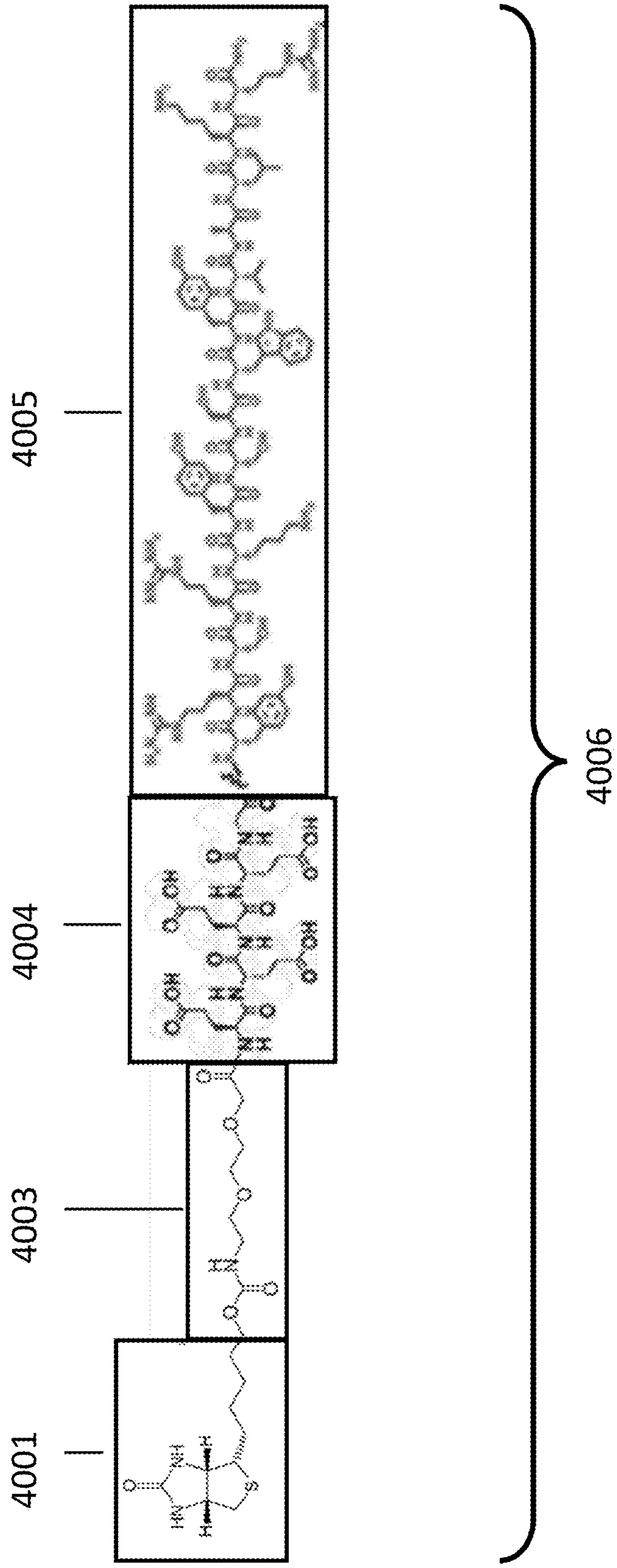
FIG. 4 shows another example of a neuronal recovery activator (NRA).

FIG. 4 depicts an example of a neuronal recovery activator [4006] comprising a linker [4001] to a cognate ligand, an optional linker sequence [4003], an optional linker peptide sequence [4004], and a neurotrophic factor peptide sequence [4005] that functions as a neurotrophic factor or bioactive molecule. In this example, the linker [4001] is biotin, the designated cognate ligand (not depicted) is streptavidin or neutravidin, the linker sequence [4003] is a mini-polyethylene glycol (PEG), the linker peptide sequence [4004] is EEEEG, and the neurotrophic factor peptide sequence [4005] is YRSRKYSSWYVALKR, also known as fibroblast growth factor2 (FGF-2) mimetic signal peptide. An NRA may comprise one or more peptide amphiphile supramolecular polymer subunits and may be capable of self-assembling into fibrils or other types of structures.

Figure 5:
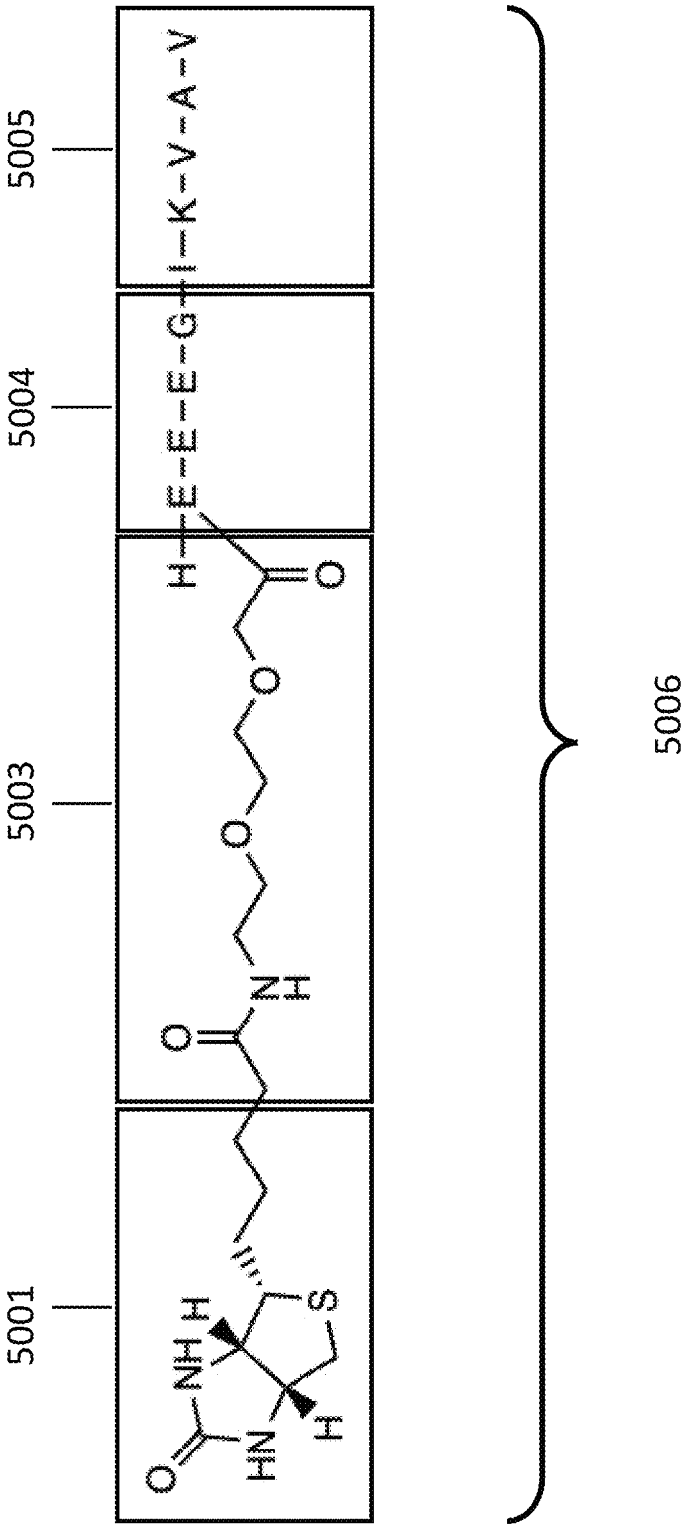
FIG. 5 shows another example of a neuronal recovery activator (NRA).

FIG. 5 depicts an example of a neuronal recovery activator [5006] comprising a biotin linker [5001], a mini-PEG linker [5003], a linker peptide sequence EEEG [5004], and a neurotrophic factor peptide sequence IKVAV [5005].

Figure 6:
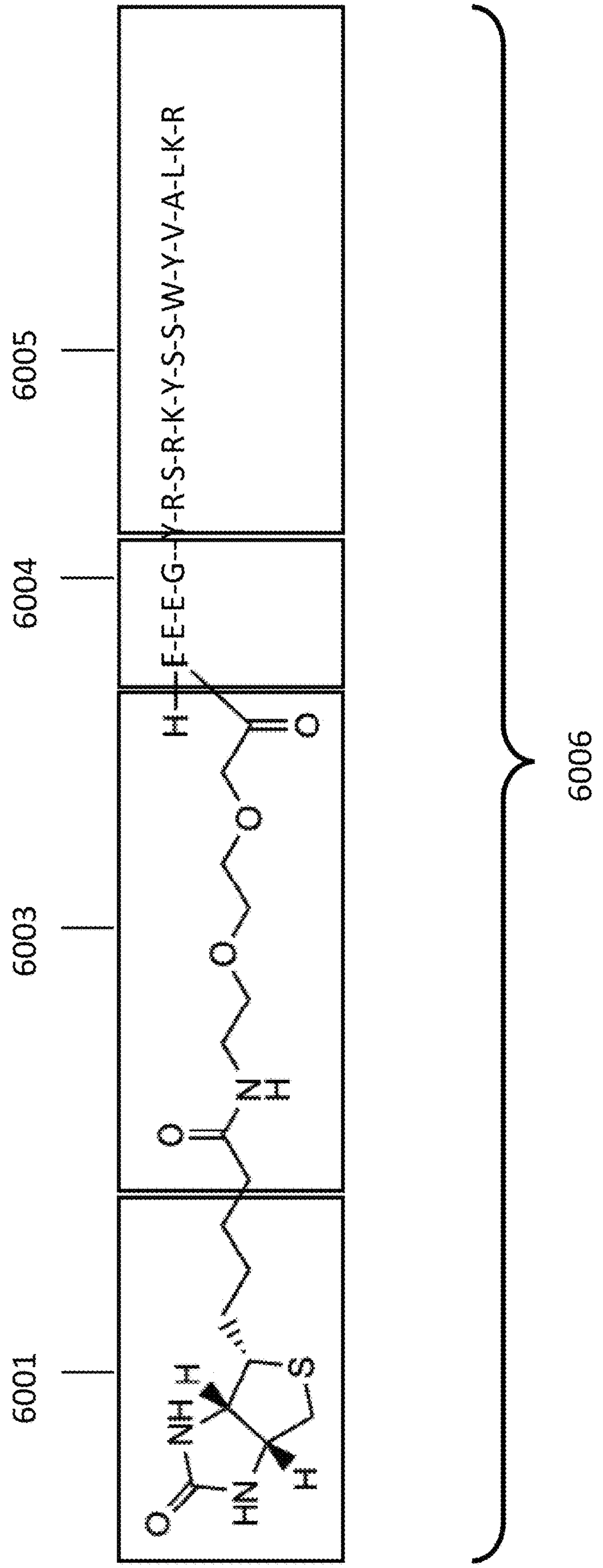
FIG. 6 shows another example of a neuronal recovery activator (NRA).

FIG. 6 depicts an example of a neuronal recovery activator [6006] comprising a biotin linker [6001], a mini-PEG linker [6003], a linker peptide sequence EEEG [6004], and a neurotrophic factor peptide sequence YRSRKYSSWYVALKR [6005].

Figure 7:
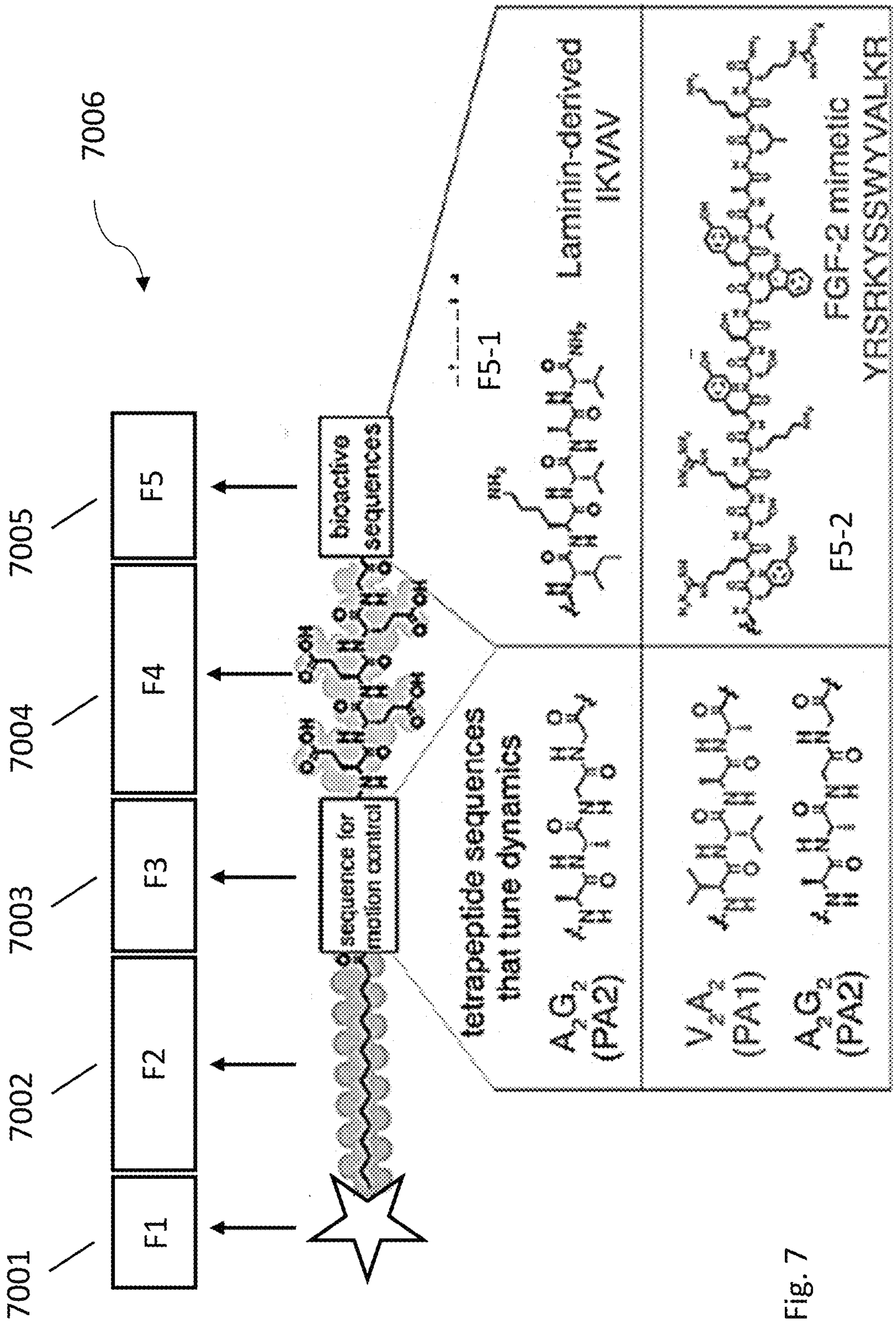
FIG. 7 shows two examples of neuronal recovery activators (NRAs).

FIG. 7 depicts an example of combinations of neuronal recovery activators [7006] comprised of a biotin linker [7001] (subunit F1), an alkyl chain [7002] (subunit F2), three versions of flexible tetrapeptide linker sequences

[7003] (subunits F3), a linker peptide sequence EEEG [7004] (subunit F4), and a neurotrophic factor peptide sequences IKVAV and YRSRKYSSWYVALKR [7005] (subunits F5-1 and F5-2). Combinations as depicted here can be used together. Subunits F3 [7003] and F4 [7004] may comprise a variety of peptide sequences (i.e. flexible tetrapeptide linker sequences or linker peptide sequences) that are useful to tune the flexibility, molecular dynamics and water solubility of the polymer, such as AAGG, VVAA, AAGG, EEEE, EEEG, EEEEG, or others listed below. Other combinations known in the art can also be used. The entire complex [7006] is an example of a neuronal recovery activator (NRA) that forms a neuronal growth activating complex (NGAC) when attached or cross-linked to particles, including magnetic particles, or to fibers, for example through a biotin linker to its designated cognate ligand streptavidin or neutravidin.

Figure 8:
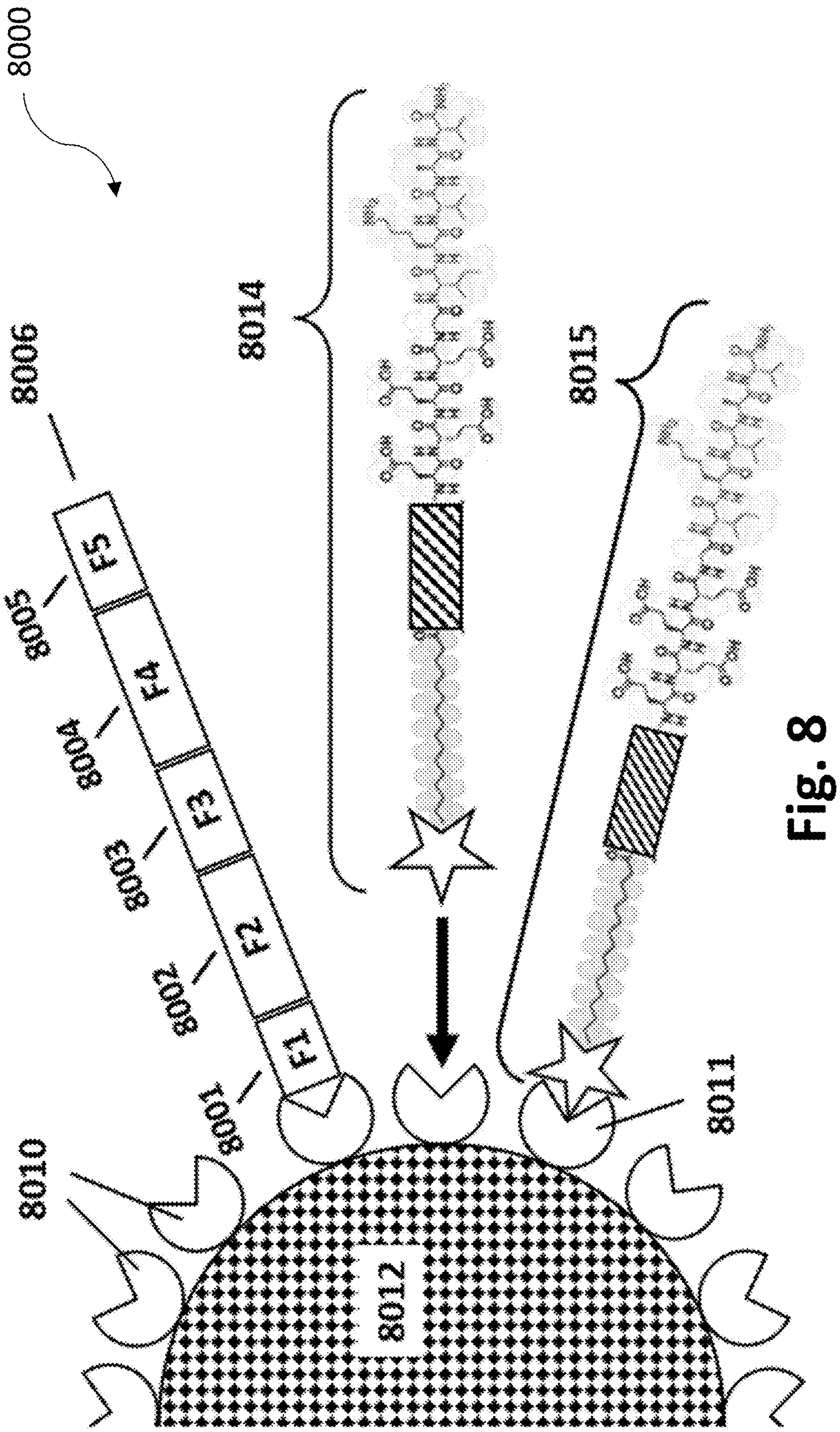
FIG. 8 shows an example of a neuronal growth activating complex (NGAC).

FIG. 8 depicts an example of a neuronal growth activating complex (NGAC) comprising neuronal recovery activators [8006], [8014] and [8015] comprised of biotin linkers [8001] (subunit F1), alkyl chains [8002] (subunit F2), flexible tetrapeptide linker sequences [8003] (subunit F3 and cross-hashed boxes), linker peptide sequences [8004] (subunit F4), and a neurotrophic factor peptide sequence IKVAV [8005] (subunit F5). Neuronal recovery activator [8006] is shown schematically as bound to a cognate ligand streptavidin [8010] to a magnetic particle [8012]. Neuronal recovery activator [8014] is shown as not yet bound. Neuronal recovery activator [8015] is shown as bound to streptavidin [8011] on the magnetic particle [8012].

Figure 9:
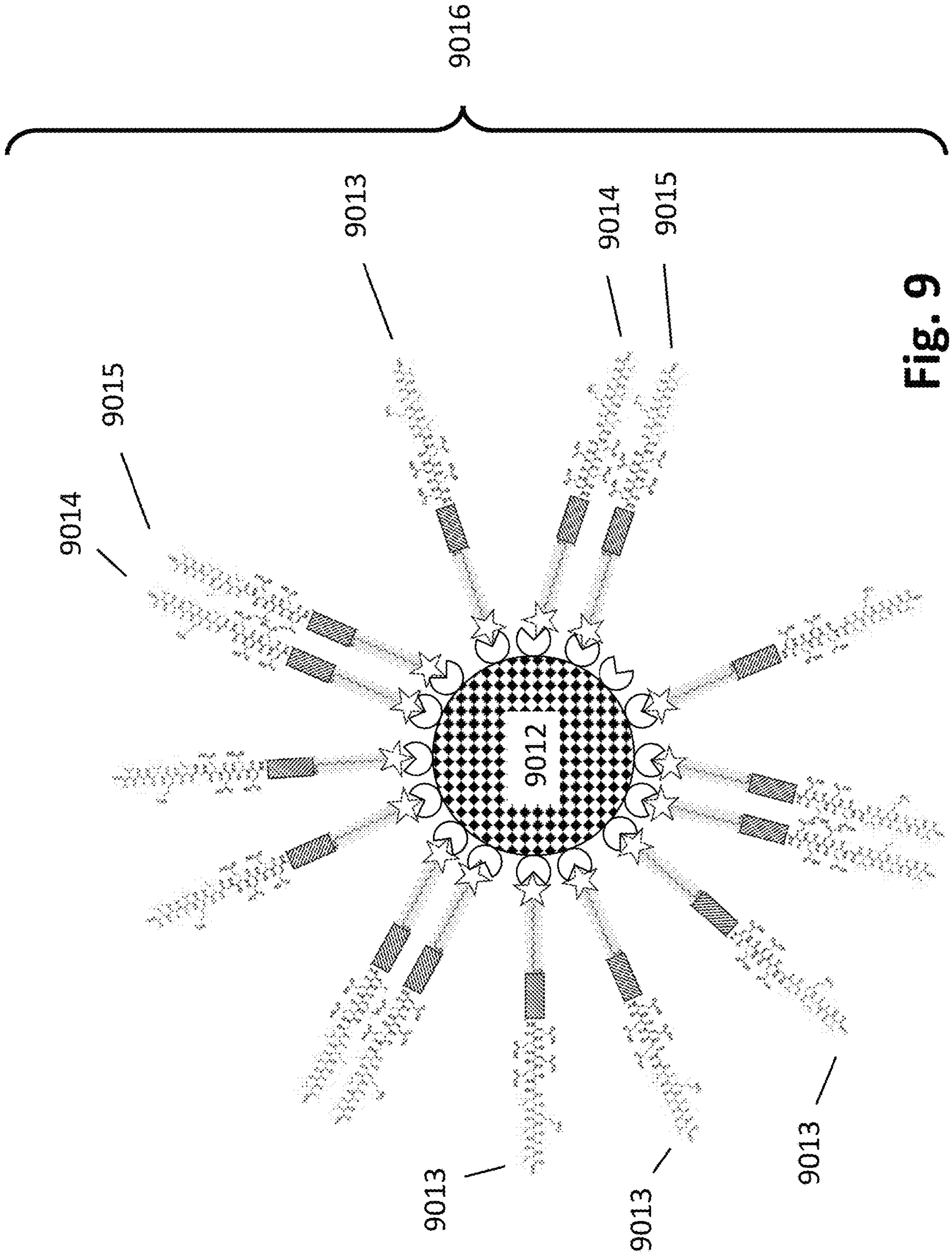
FIG. 9 shows another example of a neuronal growth activating complex (NGAC).

FIG. 9 depicts an example of a neuronal growth activating complex (NGAC) comprising multiple neuronal recovery activators (NRAs) such as [9013], [9014] and [9015] bound to a particle [9012] via biotin-streptavidin linkages, as shown in more detail in FIG. 8. Peptide amphiphile structures [9014] and [9015] are shown to form beta sheets while bound to the surface of the particle, whereas peptide amphiphile structures [9013] do not. The addition of peptide amphiphile structures to a particle, such as a magnetic particle, may occur before or after particles are aligned into fibers or structures for neuronal guidance.

Figure 10:
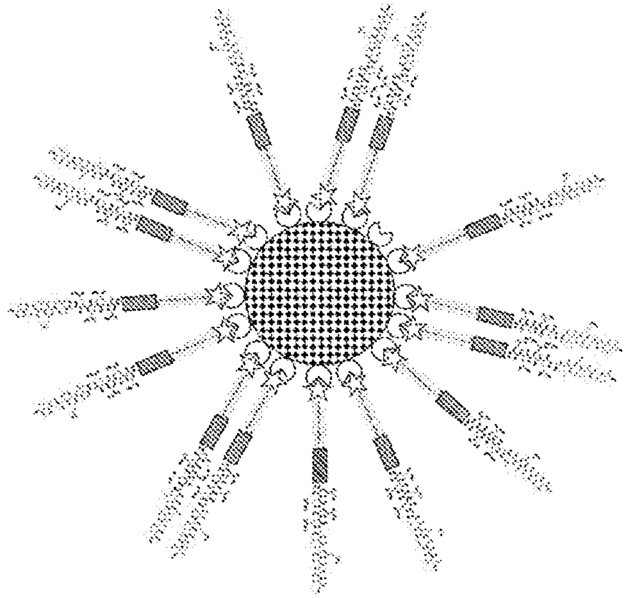
FIG. 10 shows an example of multiple neuronal growth activating complexes (NGACs) forming a fiber consisting of aligned individual NGACs.

FIG. 10 depicts an example of a neuronal growth activating complex (NGAC) [10016], also shown in highly schematic form as [10017] and [10018]. [10019] denotes a magnetically formed fiber consisting of aligned individual NGACs [10018] (here N=16). Some peptide amphiphile structures of the neuronal recovery activators (NRAs) are shown to form beta sheets while bound to the surface of the particle. The addition of neuronal recovery activators or peptide amphiphile structures to a particle may occur before or after particles are aligned into fibers. An externally applied magnetic field can be used to align NGACs into fibers [10019] through magnetic moments of magnetic particles that are part of the NGACs.

Figure 11:
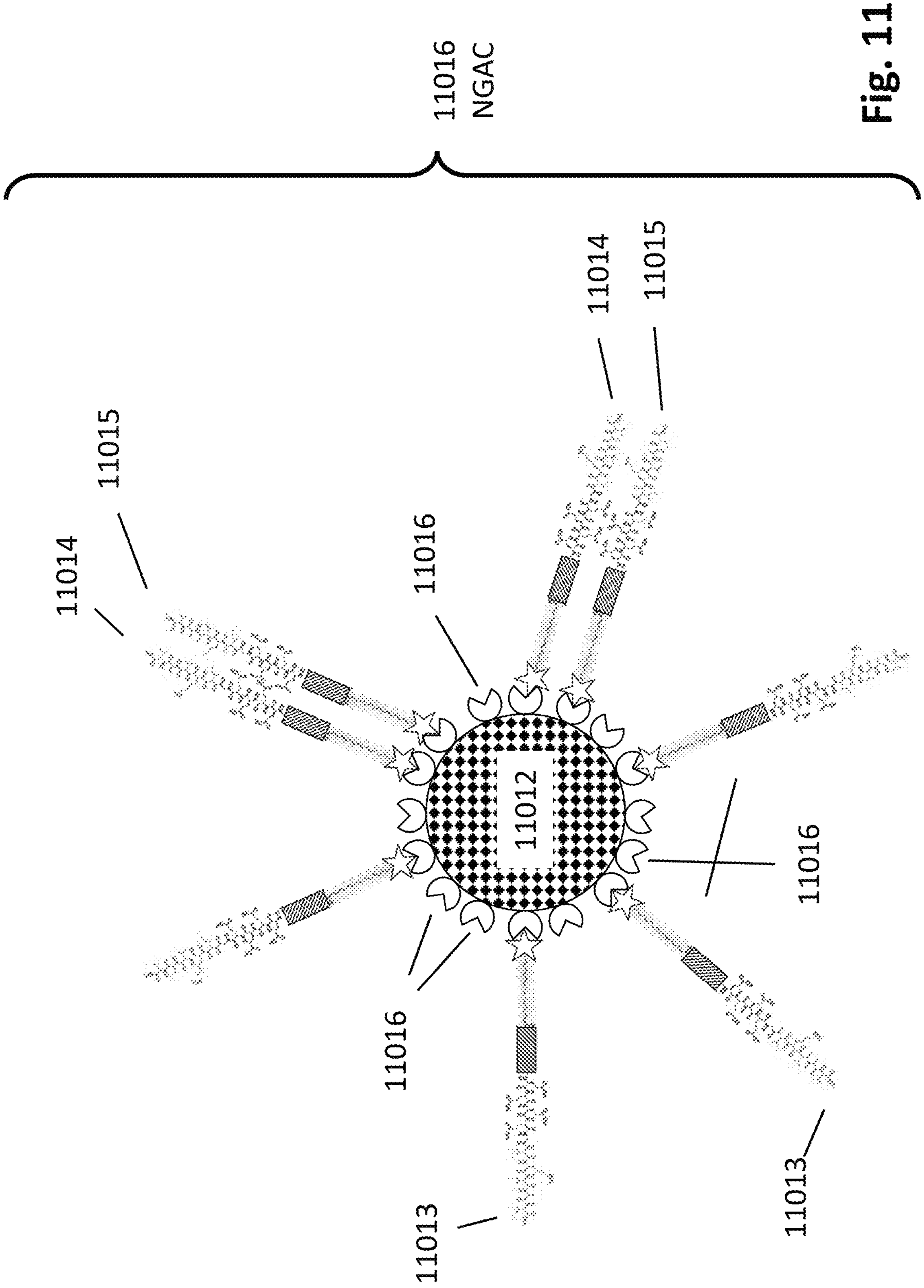
FIG. 11 shows another example of a neuronal growth activating complex (NGAC).

FIG. 11 depicts denotes individual NRAs comprising peptide amphiphile structures [11013], [11014] and [11015] bound to a magnetic particle [11012]. Peptide amphiphile structures [11014] and [11015] are shown to form beta sheets while bound to the surface of the particle, whereas peptide amphiphile structures [11013] do not. Note the availability of free cognate ligands [11016], such as streptavidin or neutravidin, on the magnetic particle [11012]. The functionalization of the magnetic particle [11012] with NRAs and peptide amphiphile structures has a reduced density compared to FIG. 9 in order to allow for optional crosslinking while utilizing the same binding moieties on the particle that bind to the ligand moiety [7001] (subunit F1) of FIG. 7.

Figure 12:
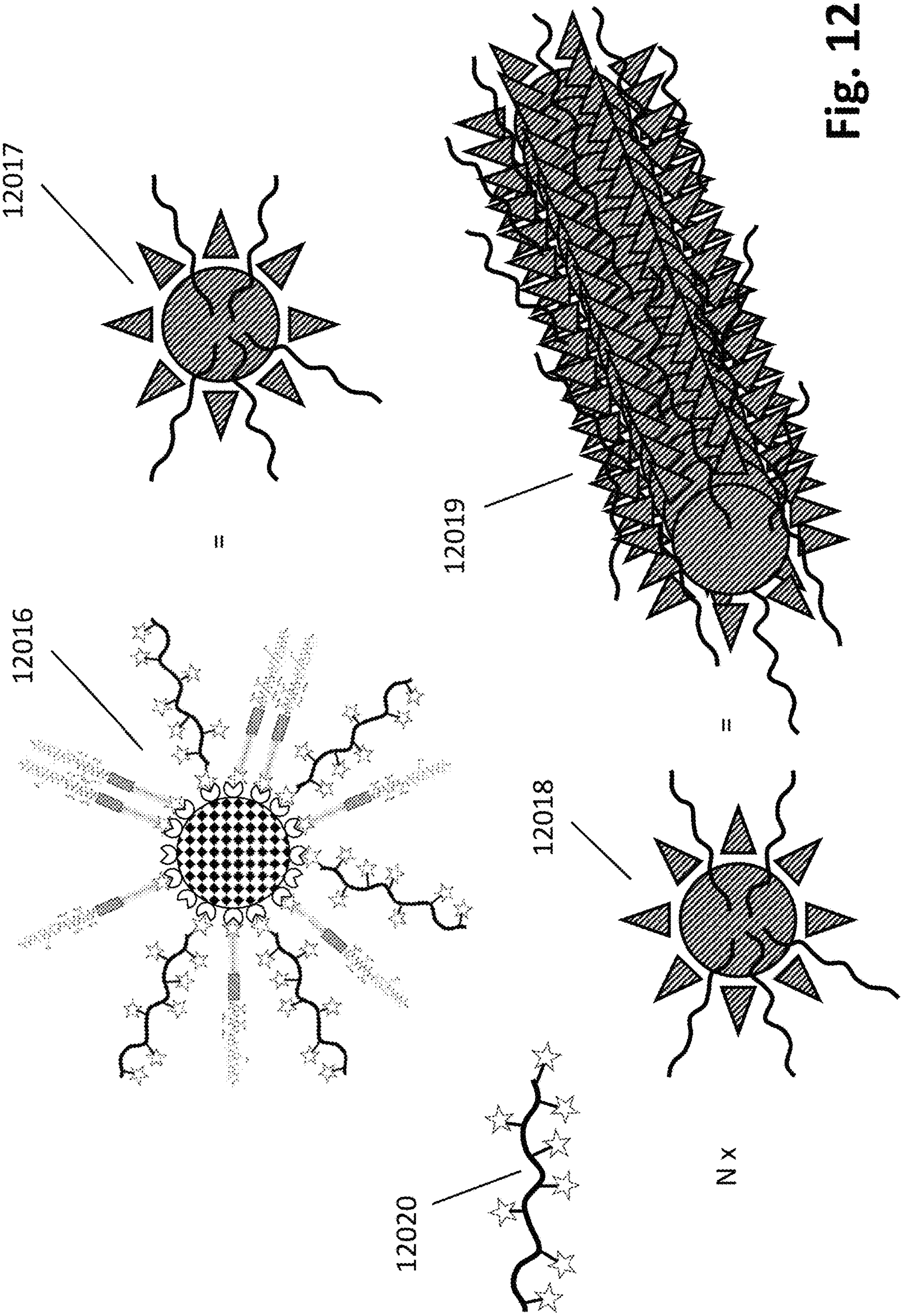
FIG. 12 shows an example of multiple neuronal growth activating complexes (NGACs) forming a fiber comprising aligned individual magnetic particles crosslinked by biotinylated DNA molecules.

FIG. 12 depicts denotes a segment of biotinylated DNA [12020] that is combined with an NGAC as depicted in FIG. 11 to form a modified NGAC [12016] that comprises NRAs as well as biotinylated DNA that are bound to cognate ligands on the magnetic particle. The modified NGAC [12016] is again depicted in highly schematic form denotes a magnetically formed fiber consisting of aligned individual modified NGACs (here N=16) that include multiple biotinylated DNAs [12020], where the biotinylated DNA [12020] molecules present on adjacent modified NGACs and magnetic particles bind to other cognate ligands on NGACs and magnetic particle in the vicinity, thereby crosslinking proximal NGACs and magnetic particle into fibers [12019]. This crosslinking allows for a magnetic field to be removed after the formation of fibers or other desired structures and maintaining the integrity of the fibers or other desired structures. The addition of biotinylated DNA to NGACs or particles may occur before or after particles are aligned into fibers.

Figure 13:
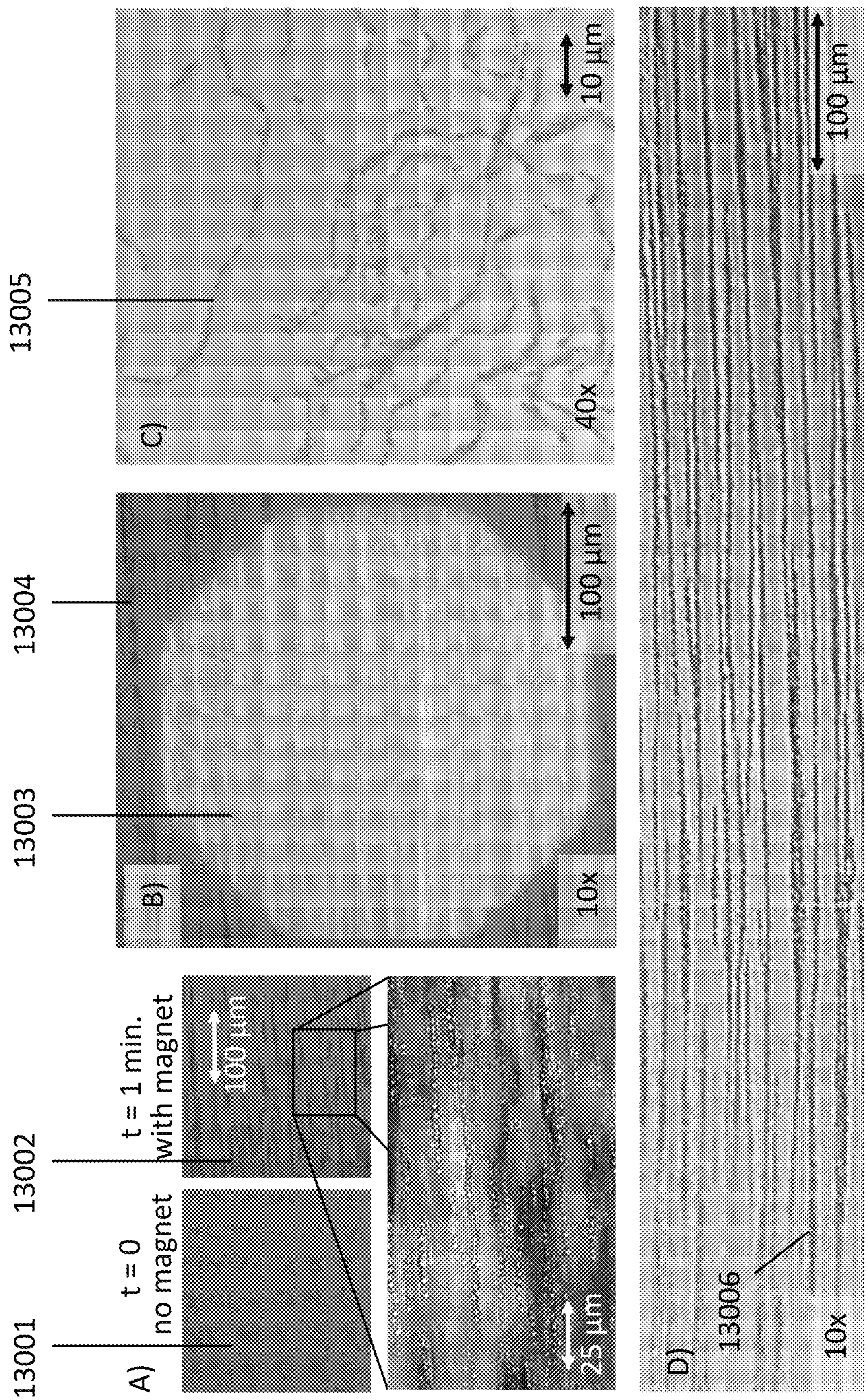
FIG. 13 shows various forms of fibers and fiberguides comprising chains of magnetic particles.

FIG. 13 depicts various forms of fibers, or fiberguides, comprising chains of magnetic particles or NGACs. FIG. 13A) shows individual magnetic particles [13001] (upper left panel in FIG. 13A) in the absence of a magnetic field self-assembling into horizontal fiberguides [13002] (upper right panel in FIG. 13A) within about 1 minute after the application of an external magnetic field in a hydrogel-based microenvironment. The lower panel in FIG. 13A) is a magnified section of the upper right panel in FIG. 13A with individual magnetic particles or NGACs visible that make up the fiberguides. After crosslinking and stabilization of the magnetic particles or NGACs, the aligned fibers or fiberguides persist for weeks in both 2D or 3D environments. FIG. 13 B) shows fiberguides [13003] on the surface of a polystyrene petri dish and crosslinked by biotinylated DNA and stained with SYBR green I (center section, [13003]). Fiberguides [13004] are visible too but not located in the center of the illuminated sample. The appearance of the aligned fibers or fiberguides is unchanged two weeks after their formation and after the subsequent removal of the external magnetic field (10× magnification). FIG. 13 C) shows details of fiberguides [13005] in a 3D environment after cross-linking with biotinylated DNA and removal of the external magnetic field, but before stabilization in 3D has occurred. Individual magnetic particles or NGACs can be seen to continue to adhere together in chains and similar structures, but the common orientation of the fiberguides (now flexible chains) when a magnetic field was applied is gradually lost due to diffusion and convection (40× magnification). FIG. 13 D) shows extended fiberguides [13006] in a 3D environment after spatial stabilization in a 3D microenvironment or neurotrophic microenvironment has occurred.

Figure 14:
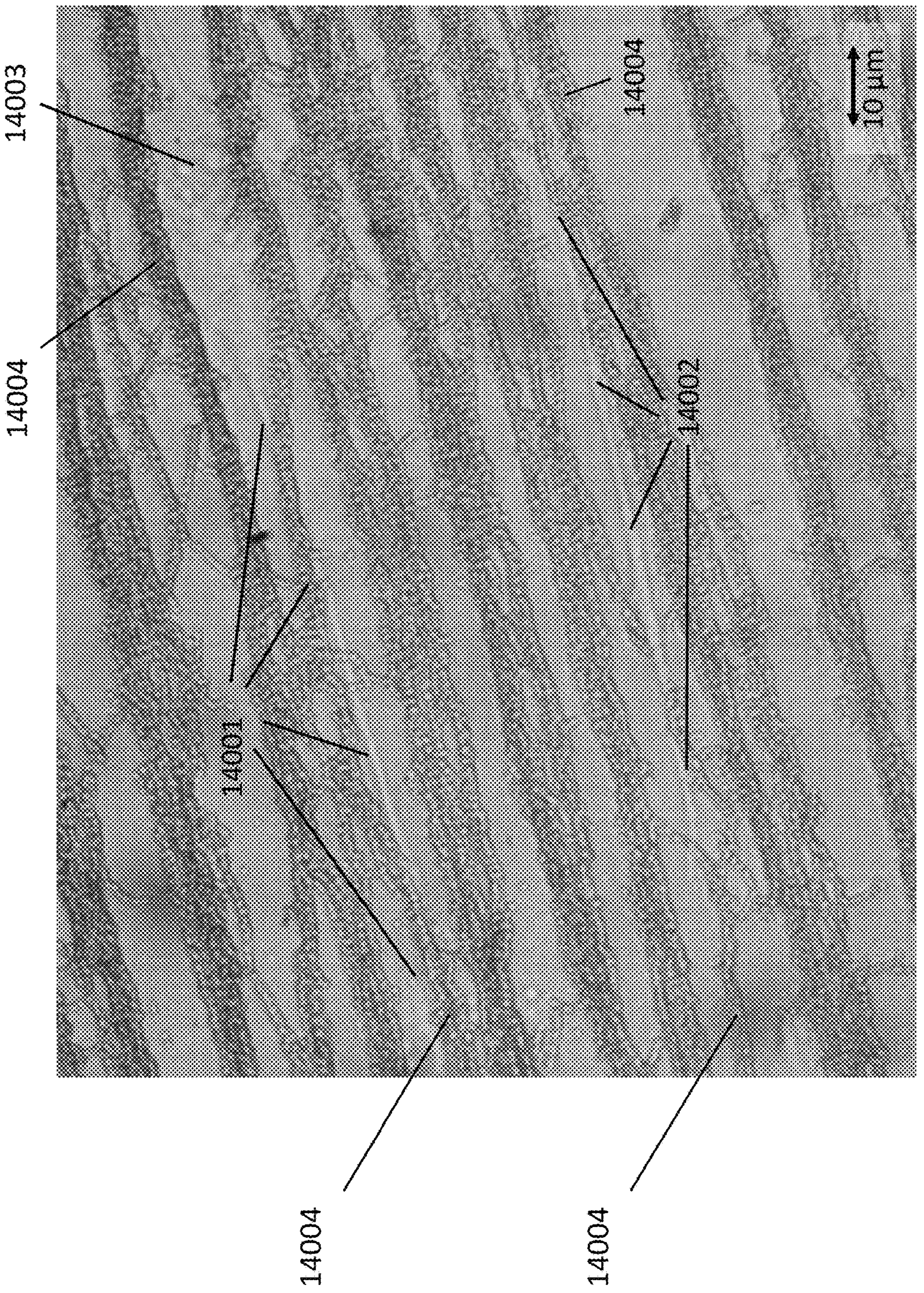
FIG. 14 shows guided growth of axonal extensions along magnetically formed fiberguides comprising magnetic particles.

FIG. 14 depicts guided growth or neurites or axonal extensions along magnetically formed fiberguides comprising magnetic particles or NGACs. Two separate axonal extensions [14001] and [14002] from two N1E-115 cells [14003] follow the general direction of fiberguide bundles [14004]. Only one cell body of a single N1E-115 cell [14003] is visible, forming axonal extension [14001] in a direction towards the left. The second N1E-115 cell, forming axonal extension [14002] also towards the left, is located out of the frame to the right of the image.

Aqueous formulation comprising magnetic particles, bioactive molecules and a neurotrophic microenvironment Prepare 9.2 mM stock solutions each of one or more neuronal recovery activators (NRAs) (LifeTein, LLC, Somerset, NJ), comprising a synthetic biotinylated neurotrophic factor peptide in protease-free deionized water. In this example, two NRAs are used: Biotin-{mini-PEG}-EEEG-IKVAV, hereinafter called “221116-262”, and Biotin-{mini-PEG}-EEEG-YRSRKYSSWYVALKR, hereinafter called “221116-422” (see FIG. 5 [5006] and FIG. 6 [6006]). Combine aliquots of both for a combined solution containing 4.6 mM of each NRA, 221116-262 and 221116-422, in protease free DI water. Dilute 2000-fold in protease-free deionized water. Dilute 10-fold in phosphate buffered saline (PBS) or culture medium (1% penicillin streptomycin, 5% fetal bovine serum in Opti-MEM™ I Reduced Serum Medium (ThermoFisher), 0.22 micrometer sterile filtered).

Functionalize magnetic particles (GBLG beads, Neuropair, Princeton, NJ) for a 1% coating of available biotin binding sites with the two NRAs 221116-262 and 221116-422: Place 400 µl GBLG beads on a magnetic separation stand. Magnetically collect the beads, remove and discard supernatant. Remove GBLG beads from magnetic separation stand. Resuspend GBLG beads in 200 µl of PBS (or culture media) containing the NRAs 221116-262 and 221116-422 by quickly vortexing for 2 minutes to result in about 1% of available streptavidin binding sites on the GBLG beads being functionalized with two NRAs 221116-262" and 221116-422, resulting in an neuronal growth activating complex (NGAC) (see FIG. 8, FIG. 9 [9016], FIG. 11 [11006]).

Optionally add 20 µl of about 10 nM biotinylated DNA (synthetically made from human, bacteriophage Lambda or another template organism, or from an artificial sequence template, a PCR product template, or a from whole-genome amplified (WGA) DNA template), preferably with an average length of about 1000-10,000 basepairs, as a magnetic particle/NGAC crosslinking and fiber scaffold stabilization reagent (see FIG. 12 [12020]).

Add 200 µl of a hydrogel (i.e. a hyaluronic acid hydrogel, such as HA HyStem (Advanced Biomatrix, San Diego, CA), a photocrosslinkable a hyaluronic acid hydrogel (Advanced Biomatrix), PureCol® EZ Gel (Advanced Biomatrix), or a hydrogel containing 2 mg/ml collagen), mix immediately, transfer/insert/inject into the desired location and apply an external magnetic field so as to magnetically align the magnetic particles and NGACs comprising in the magnetic particles into fibers or fiberguides (see FIG. 12 [12019]). Allow the biotinylated DNA to crosslink the aligned NGACs with the enteral magnetic field in place, thereby stabilizing the fibers or fiberguides. Optionally remove the enteral magnetic field.

The hydrogel is preferably liquid and non-crosslinked when it is mixed with the NGACs to allow for efficient mixing before NGACs are magnetically aligned and before the biotinylated DNA crosslinks the aligned NGACs. This step should therefore be done quickly and immediately before use, prior to the formation of fibers through the application of an external magnetic field. Alternatively, other types of hydrogels can be used, including pre-crosslinked hydrogel structures in suspension that can be transferred/inserted/injected through a fine needle. Average sizes of such pre-crosslinked injectable hydrogel structures may range from 10-100 nm (nanometer), 100-1000 nm, 1-10 µm (micrometer), 10-100 µm, 100-1000 µm, and a combination thereof. Preparation of suitable hydrogels made from powderized matrix materials that function as a neurotrophic microenvironment have been described in the literature. One example is a hydrogel prepared from decellularized, ground porcine omentum as described in (Wertheim, 2002). Similar hydrogel preparations and other matrix- or scaffold-forming materials capable of forming a neurotrophic microenvironment can also be used (Fan B, 2018; Chan S J, 2017; Keefe K M, 2017; Muheremu, 2021; Santos, 2016; Richard S A, 2021; Liu D, 2021; Liu X, 2022; Chakravarty S, 2015; Kubinová S, 2012; Joshi, 2017; Jiao G, 2017; Han S, 2015; Grous 2013; Woods I, 2022; Wang L, 2020; Tukmachev D, 2016; Wen Y, 2016). A combination of any of those hydrogel preparations can also be used and are incorporated herein by reference in their entirety.

Where a term is provided in the singular, the inventors also contemplate aspects of the invention described by the plural of that term. As used in this specification and in the appended claims, the singular forms “a”, “an” and “the” include plural references unless the context clearly dictates otherwise, e.g., “a tip” includes a plurality of tips. Thus, for example, a reference to “a method” includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods, constructs and materials are now described. All publications mentioned herein are incorporated herein by reference in their entirety. Where there are discrepancies in terms and definitions used in references that are incorporated by reference, the terms used in this application shall have the definitions given herein.

The current invention builds on the Fibermag approach by adding specific novel combinations of bioactive molecules, neurotrophic factors and microenvironments.

The signaling of cells by scaffolds of synthetic molecules that mimic proteins has been known to be effective in the regeneration of tissues. Peptide amphiphile supramolecular polymers containing two distinct signals (peptide sequences) have been shown to activate the transmembrane receptor B1-integrin and a second one activates the basic fibroblast growth factor 2 receptor (Alvarez, 2021). Mutating the neurotrophic factor peptide sequence of the amphiphilic monomers in non-bioactive domains can intensify the motions of molecules within scaffold fibrils or fibers. This results in notable differences in vascular growth, axonal regeneration, myelination, survival of motor neurons, reduced gliosis, and functional recovery, indicating that the signaling of cells by ensembles of molecules can be optimized by tuning their internal motions.

The application of static or changing/modulated/oscillating magnetic fields has also been shown to affect cellular signaling, behavior and stimulated growth (Seo, 2013; Guo, 2016). Devices by Orthofix in the UK are approved for clinical use in humans to speed up the healing of bone fractures, and devices for hyperthermia treatment are approved to treat certain cancers. Surprisingly, the effects of an electromagnetically applied field can also extend to individual cells when they are exposed to magnetic nanoparticles typically used for hyperthermia applications even though under those conditions no significant elevation in temperature can be induced (Rodriguez-Luccioni, 2011). Oscillating magnetic fields can improve cellular signaling, behavior and stimulate growth.

The present invention combines the beneficial and growth-inducing effects of cellular activation, growth stimulation and directed growth through the effects of aligned fiber scaffolds, biological microenvironments, or supporting gel matrices that are surface functionalized with agents bioactive molecules and neurotrophic factors such as 'neuronal recovery activators' (NRAs). NRAs may comprise peptide amphiphile supramolecular polymers (PAs). Bioactive molecules and neurotrophic factors may preferably comprise the peptide sequences IKVAV and YRSRKYSSWYVALKR. Scaffolds that have been described in the prior art are non-directional, unaligned and typically self-form from amphiphile peptide subunits.

This invention describes methods to extend and further enhance the benefits of cellular activation by NRAs by additionally providing an aligned scaffold and a neurotrophic microenvironment. An aligned scaffold can comprise one or more NRAs and self-assembling fibers/fibrils as described in (Alvarez, 2021). NRAs or PAs comprising NRAs can be attached or cross-linked to particles, including magnetic particles, or to fibers by functionalization of the particles or fibers through various types of binding and ligand/receptor combinations. The resulting complex is hereinafter called neuronal growth activating complex (NGAC). Particles or fibers can be magnetic or non-magnetic. Functionalization can optionally be performed before or after the formation or alignment of particles or fibers into a parallel scaffold in the injury site.

In some preferred embodiments, the general invention method comprises an earlier step of functionalizing surfaces of the particles or fibers with one or the more chemical moieties prior to administering an aqueous formulation comprising the particles or fibers to the damaged neural tissue in the patient, wherein the surfaces of the particles or fibers are functionalized with the one or more moieties selected from the group consisting of streptavidin, neutravidin, antibodies, antigens, ligands, biotin, laminin, fluorescein, psoralen, methyl methacrylate, avidin, DNA hybridization molecules, DNA origami, DNA dendrimers, aptamers, protein, metal ion chelators, His tags, polyethylene glycol linkers, 'mini-PEG' linkers, agarose, acrylamide, collagen, phase transfer catalysts, and any combination thereof.

In other preferred embodiments, the general invention method further comprises an earlier step of functionalizing the surfaces of the particles or fibers with the one or more chemical moieties is for promoting a chemical bonding between the particles or fibers when the magnetic field is aligning the particles or fibers and forming the one or more aligned chains of the particles or fibers parallel to the nerve fiber.

In some invention method embodiments, an aqueous formulation comprising the particles or fibers further comprises a molecule selected from the group consisting of a neuronal cell growth factor, a chemotactic factor, a cell proliferation factor, a directional cell growth factor, a neuronal regeneration signaling molecule, a laminin, an inhibitor of glial cell induced scar formation, an inhibitor of astrocyte cell induced scar formation, an inhibitor of oligodendrocyte cell induced scar formation, an inhibitor of astrocyte precursor cell induced scar formation, an inhibitor of oligodendrocyte precursor cell induced scar formation, an inhibitor of 4 sulfation on astrocyte derived chondroitin sulfate proteoglycan, an inhibitor of chondroitin sulfate proteoglycan phosphacan, an inhibitor of chondroitin sulfate proteoglycan neurocan, a chondroitinase ABC, an inhibitor of chondroitin sulfate proteoglycan 4, an inhibitor of neuron glial antigen 2, an antibody to chondroitin sulfate proteoglycan 4, an antibody against neuron glial antigen 2, an inhibitor of glial cell expression of chondroitin sulfate proteoglycan 4, an inhibitor of glial cell expression of neuron glial antigen 2, an inhibitor of keratan sulfate synthesis, an inhibitor of glial cell expression of an enzyme involved in keratin sulfate synthesis, an inhibitor of an oligodendritic cell debris origin neuroregeneration inhibiting protein, an inhibitor of a glial cell debris origin neuroregeneration inhibiting protein, an antibody against myelination inhibitory factor NI 35, an antibody against myelination inhibitory factor NOGO, an anti oxidants, cerium oxide particles, an amino acid, a phospholipid, a lipid, a vitamin, an anticoagulant, and a combination thereof.

In some invention method embodiments, the aqueous formulation comprising the particles or fibers further optionally comprises a carrier which is microspheres, porous particles, a gel, a hydrogel, a multiphase solution, a colloid, a capsule, a microcapsule, a liposome, an isotonic saline, a cerebrospinal fluid, or a combination thereof.

In other preferred embodiments, the general invention method further comprises the step of stabilizing the aligned chains of the particles or fibers in the magnetic field using a cross linking polymer architecture for locking the aligned chains of the particles or fibers into place after using a magnetic field for aligning the particles or fibers and forming one or more aligned chains of the particles or fibers in the magnetic field as the scaffold to guide directional growth of regenerating nerve cells.

In other preferred embodiments, the general invention method further comprises the step of stabilizing the aligned chains of the particles or fibers in the magnetic field using a cross linking polymer architecture for locking the aligned chains of the particles or fibers into place after the step of using the magnetic field for aligning the particles or fibers in the orientation which is parallel to the nerve fiber orientation in the damaged neural tissue and forming the one or more aligned chains of the particles or fibers in the magnetic field in the orientation which is parallel to the nerve fiber orientation in the damaged neural tissue, and before the step of using the one or more aligned chains of the particles or fibers in the orientation which is parallel to the nerve fiber orientation in the damaged neural tissue as a scaffold for regenerating the nerve fiber in the damaged neural tissue of the patient. In some invention method embodiments, the aligned chains of the particles or fibers that are the scaffold for regenerating the nerve fiber in the damaged neural tissue of the patient are stabilized by a cross linking polymer architecture.

In some invention method embodiments, the cross-linking polymer architecture for forming or stabilizing NGAC or aligned chains of the particles or fibers is selected from the group consisting of a cross linking homopolymer of the surface functionalized magnetic particles, a cross linking copolymer of different surface functionalized magnetic particles, a cross linking junction controlled branched polymer of the surface functionalized magnetic particles, and a combination thereof.

In some invention method embodiments, the cross linking polymer architecture for forming or stabilizing NGAC or the aligned chains of the particles or fibers is formed using molecules selected from the group consisting of psoralen, methyl methacrylate, avidin, streptavidin, antibodies, antigens, ligands, biotin, laminin, fluorescein, DNA hybridization molecules, DNA origami, DNA dendrimers, aptamers, protein binding, protein DNA binding, metal ion chelators, His tags, polyethylene glycol linkers, agarose, acrylamide, collagen, phase transfer catalysts, and any combination thereof.

Some invention method embodiments further comprise the step of removing the magnetic field which is parallel to the nerve fiber orientation after the step of forming or stabilizing NGAC or the aligned chains of the particles or fibers using the cross linking polymer architecture.

In some invention method embodiments, the particles or particles or fibers have dimensions selected from the group consisting of between about 10 nm (nanometers) to 20 nm in diameter, between about 20 nm to 50 nm in in diameter, between about 50 nm to 100 nm in diameter, between 100 nm to about 1 micrometer, between about 1 micrometer to about 20 micrometer in diameter, between about 2 micrometer to about 40 micrometer in diameter, between about 3 micrometer to about 10 micrometer in diameter, between about 1 micrometer to about 15 micrometer in diameter, between about 0.05 micrometer to about 100 micrometer in diameter, between about 5 micrometer to about 500 micrometer in diameter, and a combination thereof.

In some invention method embodiments, a magnetic field used to align the magnetic particles or the magnetic fibers has a strength between about 0.1 Gauss to 1 Gauss, between about 1 Gauss to 5 Gauss, between about 5 Gauss to 10 Gauss, between about 10 Gauss to 20 Gauss, between about 20 Gauss to 50 Gauss, between about 5 milli Tesla to about 50 milli Tesla, between about 50 milli Tesla to about 100 milli Tesla, between about 100 milli Tesla to about 500 milli Tesla, between about 0.5 Tesla to about 2 Tesla.

In some invention method embodiments, magnetic fibers (either pre-existing fibers or fibers magnetically formed from chains of particles) are moved laterally towards severed nerve endings through the use of a magnetic field gradient, which can be applied temporarily or permanently, either to the partially or fully formed magnetic fibers or fiberguides, or to the magnetic particles before or during the process of their alignment into fibers or fiberguides. The benefit of this embodiment is that the magnetic particles or the resulting individual magnetic fibers or fiberguides are induced to enter available spaces between existing axons, neurons and other cells of the injured cord, more so than just by diffusion alone, and to therefore better form physical and possible electrical connections and molecular linkages between axons, neurites and neurons on one side and the growth-inducing aligned fibers on the other.

This effect of this embodiment can aid a functional reconnection because it avoids a gap, which is typically present between an implant with a comparatively blunt surface and an irregularly shaped stump of the injured spinal cord. This fluid-filled gap usually extends over several mm in at least some places, which is a significant distance for regenerating neurites and axons to overcome. In contrast, the effect provided by this embodiment not only minimizes the gap to zero but essentially makes it negative by magnetically driving the magnetic particles and fibers in between remaining nerve endings, resulting in an overlap rather than a gap that needs to be bridged.

The magnetic field gradient can be applied after or during the formation of aligned fibers from chains of magnetic particles. A magnetic field gradient may be between 0.1 Gauss/m to 1 Gauss/m, between about 1 Gauss/m to 5 Gauss/m, between about 5 Gauss/m to 10 Gauss/m, between about 10 Gauss/m to 20 Gauss/m, between about 20 Gauss/m to 50 Gauss/m, between about 5 milli Tesla/m to about 50 milli Tesla/m, between about 50 milli Tesla/m to about 100 milli Tesla/m, between about 100 milli Tesla/m to about 500 milli Tesla/m, between about 0.5 Tesla/m to about 2 Tesla/m.

The magnetic particles or the resulting individual magnetic fibers or fiberguides can further be functionalized with bioactive molecule structures that promote axonal regrowth, neuronal survival, angiogenesis and functional recovery from SCI.

Some embodiments of the invention are methods wherein the earlier step of functionalizing the surfaces of the particles or fibers with one or more chemical moieties is for forming neuronal growth activating complexes (NGAC). The invention embodiments include methods wherein the functionalized particles or fibers comprise more than one functionalization. For example, such functionalization may include several different neuronal recovery activators (NRAs), such as comprising the peptide sequences IKVAV (FIG. 1, FIG. 3-F5-1) or YRSRKYSSWYVALKR (FIG. 2, FIG. 3-F5-2). NRAs may comprise ligands for binding, attaching, stabilizing or crosslinking them to particles or fibers from the groups listed above (FIG. 3, depicted as a star, 3011). The NRAs depicted in FIG. 3 as F5 can comprise either F5-1 or F5-2 or a combination thereof. The ligands depicted in FIG. 3, F1 can comprise any ligand or binding partner of a cognate binding pair as described above, or a combination thereof. A preferred combination is biotin and streptavidin. The invention embodiments include methods wherein the earlier step of functionalizing the surfaces of the particles or fibers with the one or more chemical moieties for forming the NGAC and NRAs is conducted in the presence of a magnetic field. Another preferred combination is a first chemical moiety as a thiol and a second chemical moiety as a primary amine. Another preferred combination is a first chemical moiety as a carboxylic acid and a second chemical moiety as a primary amine.

The addition of aligned and optionally magnetically generated fibers to the unexpectedly successful approach of enhancing the intensity of molecular motions with bioactive fibrils (peptide amphiphile supramolecular polymers, NRAs) creates a new type of biophysical environment that provides directionality to axonal regeneration, enhances neuronal growth and survival, and blood vessel regeneration through a novel combination of physical and cellular signaling stimuli, resulting in probable improved and accelerated functional recovery from SCI.

Examples for aligned fibers that may comprise NRAs and can be used as NGAC are:

Biocompatible or biodegradable magnetic particles that are aligned into flexible fibers, termed 'fiberguides', through an externally applied magnetic field parallel to the intended direction of regrowth. (U.S. Pat. No. 11,083,907)

Existing, pre-formed fibers are that injected into the injury site and then aligned, for instance through the effect of an externally applied magnetic field, such as magnetic electrospun fibers, for example magnetically responsive aligned poly-1-lactic acid electrospun fiber scaffolds Preformed and aligned fiber scaffolds that are surgically implanted into the injury site. Examples for existing but non-aligned scaffolds of such a nature have reached human trials and were found to safe but not effective in inducing aligned axonal regrowth or any sign of functional recovery. Such fibers can be made from numerous different materials and combinations thereof, including Fibers or the constituting particles can be functionalized with numerous different ligands, peptides, chemicals, biomolecules, coatings, structures, materials and any of the moieties and ligands listed above and combinations thereof Aligned magnetic fibers provide internal directional guidance to neurites within a three-dimensional collagen or fibrin model hydrogel, supplemented with Matrigel. Neurites growing from dorsal root ganglion explants extend about 2-3×further on aligned fibers compared with neurites extending in a hydrogel alone.

Combined approaches as described in this invention are of interest for minimally invasive treatments for spinal cord repair, as well as for peripheral nerve repair and applications in the brain or other central nervous system. Fibers can be injected and then magnetically positioned in situ, and the aligned fiber scaffolds provide consistent topographical guidance to cells. Neuron viability is enhanced both in two-dimensional and injectable three-dimensional scaffolds. Small conduits of aligned magnetic fibers are easily injected or formed in situ by a magnetic field in a collagen or fibrinogen hydrogel solution and can be repositioned using an external magnetic field.

The ultimate product is intended to be a fast and simple therapeutic treatment for SCI, consisting of an injectable gel formulation, a device to generate a temporary magnetic field in the injury site, and a protocol for use:

The Fibermag formulation will consist of two 'just-in-time' components (particles and crosslinker/matrix) which are combined immediately before use. Mixing is done by vortexing or using a small mixing nozzle with a Luer lock connector to attach an injection needle.

The formulation is injected into the injury site of a SCI patient and an external magnetic field is applied.

Within minutes, magnetic particles align into parallel fiberguides, which automatically conform to any irregular volume of the injury and align with individual nerve endings, inducing them to grow along the desired direction. The fiberguides are stable over weeks without magnetic field. The surrounding matrix helps to block scar formation and can be infused with drugs that support regeneration (Alvarez 2021; Lima-Tenórioa, 2015; Teng, 2002). For chronic injury treatment, debridement of the existing scar would first be performed.

In one embodiment of the method, the injection of an aqueous formulation of the invention into a lesion site is used to reconnect a previously damaged nerve, even after significant scar tissue has already been formed, as for the treatment of chronic SCI. In this embodiment, the two damaged ends of the spinal cord are surgically cut further back from the initial lesion in order to generate a 'fresh' interface of exposed nerve ends before the aqueous formulation of the invention is injected. Such treatments have been attempted for patients with chronic SCI who received a pre-fabricated, randomly ordered (not oriented) implanted scaffold. The proposed treatment has been judged as safe in multi-year preliminary clinical trials but did not yet fulfil the expectations of the sponsors. The removal of chronic scar tissue and the surgical cutting of stumps and neuronal ends at the injury site may include techniques other than using a traditional scalpel, such as mechanical, biochemical, enzymatic, chemical means, that result in the abrasion, digestion, removal or exposure of 'fresh' nerve cells. 'Fresh' here means able to form neurites and connections with other nerve cells.

In a related embodiment of the present invention, additional, healthy sections of the spinal cord are deliberately sliced from one or both ends of a large lesion site. The spinal cord slices can be placed in the lesion site at distances from each other that are short enough to allow for an effective invention formulation matrix formation and neurite growth into the spaces between successive sections. In this way even very large distances of damaged or missing nerves can be successively bridged by supporting the innervation and reconnection of the neurites formed in the injected aqueous formulation of the invention with intervening sections of the original nerve. This is embodiment is similar to the technique of 'stretching' a patient's own skin, such as done for severe burn victims, when otherwise an insufficient amount of skin would be available from the patient itself to cover the entire area that requires a graft. In this technique, which is typically performed with specialized and semi automated equipment designed for only this purpose, a certain amount of skin is first harvested from a patient and then deliberately cut with hundreds of mm sized, alternating and parallel oriented incisions. The skin graft is then carefully stretched in the direction perpendicular to the cuts before applying it to the patient. The body of the patient is typically able to successfully attach the graft as if it were a non treated patch of the patient's own skin because the small distance (on the order of mm) between neighboring intact sections of skin allow their epithelial cells to extend into and eventually fully fill the small open areas, just like they would do in a small cut wound. The technique is able to cover a graft of several times the area than compared to what would be able with untreated skin grafts.

The magnetic nanoparticle-infused hydrogel, the protocol, and the magnetic field design are all potential products resulting from this proposal.

Fibermag will provide several advantages over other existing and proposed scaffold-based treatments:

(1) in situ formation after injection that matches the shape of the injury site
(2) comparatively simple and fast to administer
(3) fiberguides remain flexible and are expected to both direct and stimulate axonal regeneration
(4) seamless pairing with other successful therapies (Buchli, 2005; Zorner, 2010; Bassett, 1989; Guo, 2016; Awad, 2015)

The present invention overcomes these problems by providing a method for treating a patient of spinal cord injury with an injectable formulation, hereafter called 'Fibermag', that comprises magnetic particles and a biocompatible matrix-forming compound that can be solidified by various means in situ after its injection into the lesion of the patient, such as a spinal cord lesion cavity. The magnetic particles in the Fibermag formulation are optionally paramagnetic, superparamagnetic or ferromagnetic and reorient themselves in response to an externally applied magnetic field. When the field is applied, the internal magnetic moment of the particles is amplified and gets aligned with the external magnetic field direction, which leads to a mutual attraction between neighboring magnetic particles that results in their linear alignment along the field lines.

The magnetic interaction between the particles eventually results in the formation of extended chains of magnetic particles in the direction of the field lines. Magnetic particles that are ferromagnetic, or so-called superparamagnetic particles that retain a remnant magnetic moment after being temporarily exposed to a sufficiently strong external magnetic field, are suitable for use with this invention provided that they are resuspended before use in order to temporarily break up particle clusters and complexes that may have formed spontaneously, and so that the individual magnetic particles are available for the generation of aligned magnetic chains and fibers when an external magnetic field is applied. In some embodiments it can be advantageous to make use of residual ferromagnetic moments by the particles to facilitate their continued chaining and fiber formation in the absence of other means of stabilizing and maintaining the resulting magnetic fibers and their desired orientation in 3D space.

An external magnetic field is applied to the Fibermag formulation through the use of a permanent magnet or electromagnet such that the field lines are oriented parallel to the direction of the desired cellular regeneration, which is horizontal in this case. As a result, the magnetic particles that are present in the injected Fibermag formulation begin to form fibers that follow the orientation of the external magnetic field and its field lines across the lesion cavity. In some embodiments, it is desirable that the externally applied magnetic field is essentially homogeneous across the lesion cavity and does not contain any significant field gradients.

The Fibermag formulation optionally further comprises other components, such as cells, nerve cells or stem cells, that aid in neurite re growth and regeneration, and further optionally comprises cell growth factors, proteins, signaling molecules or chemicals that stimulate or aid in the growth, adhesion, proliferation of certain cells, in particular the directional growth of cells, such as nerve cells. Their function is to help guide axonal regeneration along the preferred direction in order to reconnect and repair the damaged nerve endings after a lesion. The formulation further optionally comprises a carrier for the controlled, retarded, extended or slow release of such compounds, such as porous particles, gels, capsules etc. as known in the art. These components of the formulation are embedded in a biocompatible liquid matrix with a viscosity suitable to be injected into the lesion cavity by syringe.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Definitions

Magnetic particle refers to synthetic particles that are temporarily or permanently magnetizable through the influence of a magnetic field. They can be superparamagnetic, paramagnetic, ferromagnetic or ferrimagnetic and are generally spherical but can have different shapes, such as disks, rods, cubes, cylinders, chains, sheets, or clusters. Paramagnetic refers to a substance which is very weakly attracted by a magnetic field, but not retaining any permanent magnetism in the absence of the magnetic field. Superparamagnetic refers to a form of magnetism which typically appears in ferromagnetic or ferrimagnetic particles or, depending on their composition and other factors, also in larger particles. The effect is that such particles generally (at ambient temperatures and in typical solvents and matrices, such as in water based solutions or gels or hydrogels) do not aggregate without the presence of an external magnetic field despite the relative strength of each particle's individual magnetic moment. When an external magnetic field is applied however, the random reorientation of each particle's individual magnetic moment is suppressed and forced to align parallel to the applied field. In proximity to other particles, the particles are then able to interact consistently with the magnetic moment of surrounding particles, thereby attracting each other to form parallel oriented chains and clusters. This property is highly desirable for many chemical and biochemical processes and surface chemistries where the particles are to be kept in solution without aggregation or cluster formation until a magnetic field is applied. In most cases, the induced magnetic moment of a such a particle disappears when the external magnetic field is removed. In the transition regime between superparamagnetic and ferromagnetic behavior however the particles may retain a slight magnetic moment of their own even when the external magnetic field is removed. This property can be desirable for applications where the particles are intended to stick to each other after a temporary application of a magnetic field, such as for the formation and continued maintenance of aligned chains or fibers. It is then necessary to use protocols that prevent or reverse undesirable aggregation or clustering after the particles have been magnetized. This can be achieved by vigorous mixing or vortexing. Magnetic particles suitable for this invention typically have an average diameter in an aqueous isotonic saline medium (AISM) selected from the group consisting of between about 0.5 micrometer to about 10 micrometer in diameter, between about 0.1 micrometer to about 5 micrometer in diameter, between about 1 micrometer to about 20 micrometer in diameter, between about 2 micrometer to about 40 micrometer in diameter, between about 3 micrometer to about 10 micrometer in diameter, between about 1 micrometer to about 15 micrometer in diameter, between about 0.05 micrometer to about 100 micrometer in diameter, between about 5 micrometer to about 500 micrometer in diameter, and a combination of diameters thereof. Nanoparticle is a term which typically refers to a particle size or diameter of up to one micrometer, but which has been known to range widely from between about 1 nanometer to tens of thousands of nanometers. In the present invention, the term particle is used interchangeably with the term nanoparticle.

Magnetic field for the present invention typically refers to magnetic field strengths from 1 mT (milli Tesla) to 10 T. Suitable magnetic fields can for example be generated by permanent magnets or electromagnets that are placed underneath, above, on the sides, or underneath and above the surface on which the particles are to be oriented. An example of a suitable electromagnet that creates field strengths on the order of tens of mT is a ten layer copper coil with 125 windings per layer and a height of 20 cm (i.e. from Magnetech Corporation, AEC Magnetics, Tasharina Corp, Essentra PLC). A preferred assembly is a stacked composite of two electromagnets facing each other with a gap spacer (i.e. MFG 6 12 by Magnetech Corporation) that generates magnetic flux lines perpendicular to the diameter test area. Higher field strengths on the order of hundreds of mT and greater are achieved by commercially available permanent magnetic separators (Generation Biotech, Qiagen, New England BioLabs, Thermofisher, Promega, MoBiTec, Germany) or rare earth or neodymium magnets (Supermagnete, Germany). Permanent magnets with residual magnetism field strengths of 500 mT to 2 T are commercially available.

Scaffold refers to a support used in tissue engineering which can help to mimic a 3D biological or neurotrophic microenvironment of cells or tissues or provide a supportive guide to aid and direct neural cell or neural tissue regeneration. A scaffold can include various structures such as crosslinked or non-crosslinked particles, magnetic particles, filaments, fibers, fibrils chains as well as branched, bifurcated or polymerized elements, or other oriented guidance mechanisms, such as tubes, ridges, channels, edges, walls or conduits, and a combination thereof. Elements of a scaffold can be aligned in a particular direction, usually parallel to each other, or randomly oriented with no particular direction. Typical scaffolds are non-directional, unaligned and may self-form from subunits such as from amphiphile peptide (PA) molecules.

Bioactive molecule refers to a molecule or chemical compound that leads to a defined biological or physiological effect when applied to a living organism, including organs, injury sites, tissues, cells, cell clusters. More specifically, the term usually refers to molecules that convey signals to cellular receptors, upon which certain changes or actions of a cell, a tissue, an injury site or an organism are initiated, controlled or suppressed. Bioactive molecules typically comprise soluble molecules, including growth factors, angiogenic factors, cytokines, hormones, DNA, siRNA, and drugs, which interact with and modulate the activity of a cell. They may occur naturally and they can be artificially synthesized, including in many modified and still functional variations that may mimic, improve, alter, control or block natural bioactive signaling processes.

Neurotrophic factors or neurotrophic molecules, sometimes also spelled neurotropic, and sometimes also called neurobiologics, neurotrophic factor peptides, or neurotrophic factor peptide sequences, are bioactive molecules that support the growth, survival, and differentiation of both developing and mature neurons. They typically comprise peptides or small proteins that interact with specific receptors on cell surfaces, and they can be modified in structure and composition while still performing their typical functions. This allows them to be synthetically produced and attached by linkers to various other molecules, carriers or structures, such as particles or fibers, and form self-assembling entities, in order to support the growth, survival, and differentiation of both developing and mature neurons, nerves, axons, neurites. Examples of Neurotrophic factors are described in (Dicou E, 1997; Fahnestock M, 2004; Fan B, 2018; Gordon T, 2009; Gordon T, 2016; Sharma V, 2022; Tukmachev D, 2016).

A biological microenvironment is the immediate small-scale environment in an organism, for example in an injury site, primarily comprised of cells, molecules and structures that surround and support other cells and tissues. Structures can be of natural origin, (such as extracellular matrices (ECM), nerves, neurons, neurites, axons, collagen, cells, plasma, fibrin, fibrinous clot, blood, blood clots, blood vessels, bone) or synthetic (such as particles, fibers, fibrils, tubes, channels, conduits, scaffolds), in forms that are linked, crosslinked, ordered, aligned, or oriented; or non-ordered, randomly aligned, sponge-like, granular, and a combination thereof.

A neurotrophic microenvironment is a natural or artificial biological microenvironment that promotes neurogenesis and regeneration of nervous tissue, such as the replacement of lost neurons (de novo neurogenesis) and/or the repair of damaged axons (axonal regeneration). A neurotrophic microenvironment can be part of a therapeutic strategy intended to augment the proliferation, differentiation, growth and regeneration of neuronal cells. Examples of the preparation of a neurotrophic microenvironment are described in (Wertheim, 2022; Krucoff, 2016; Fan B, 2018; Chan S J, 2017; Keefe K M, 2017; Muheremu, 2021; Santos, 2016; Richard S A, 2021; Liu D, 2021; Liu X, 2022; Chakravarty S, 2015; Kubinová S, 2012; Joshi, 2017; Jiao G, 2017; Han S, 2015; Grous 2013; Woods I, 2022; Wang L, 2020; Tukmachev D, 2016; Wen Y, 2016).

Decellularized omentum ECM (extracellular matrix) refers to a preparation of an aqueous injectable neurotrophic microenvironment prepared from decellularized omentum ECM in powderized form, such as described as being prepared from porcine omental tissue in (Wertheim, 2022).

Hydrogel refers to a water based gel generated by any one of a variety of means. There are many biocompatible materials available that are used to cure or form certain shapes in the body. A short peptide based hydrogel matrix is capable of holding about one hundred times its own weight in water. A hydrogel may be a network of polymer chains that are hydrophilic, sometimes found as a colloidal gel in which water is the dispersion medium. Hydrogels are highly absorbent (they can contain over 90% water) natural or synthetic polymeric networks. Hydrogels also possess a degree of flexibility very similar to natural tissue, due to their significant water content. Some hydrogels have the ability to sense changes of pH, temperature, or the concentration of metabolite and release a substance they are carrying and can act as a sustained release drug delivery system. Some hydrogels are comprised of cross linked polymers such as polyethylene oxide, polyAMPS and polyvinyl pyrrolidone (PVP). Wound gels can help create or maintain a moist environment. Hydrogel ingredients may include polyvinyl alcohol, sodium polyacrylate, acrylate polymers and copolymers with an abundance of hydrophilic groups. Natural hydrogel materials are being investigated for tissue engineering; these materials include agarose, methylcellulose, hyaluronan, and other naturally derived polymers. Examples are commercially available from Advanced Biomatrix and other companies.

An amphiphile molecule, or amphipath, refers to a chemical compound possessing both hydrophilic and lipophilic properties. Such a compound is called amphiphilic or amphipathic. Common amphiphilic substances are soaps, detergents, and lipoproteins, and they can spontaneously self-assemble into vesicles, micelles, tubes, sheets and other types of geometric structures. Phospholipid amphiphiles are the major structural component of cell membranes.

A peptide amphiphile (PA) refers to an amphiphile molecule that comprises a peptide segment, sometimes intended to function as a bioactive molecule or neurotrophic factor.

A peptide amphiphile supramolecular polymer refers to larger complex consisting of multiple peptide amphiphile subunits, which may be identical to each other or comprise different types of peptide amphiphile subunits. A peptide amphiphile supramolecular polymer may be intended to form fibers, fibrils, vesicles, sheets or other structures, sometimes through self-assembly. For the purpose of this invention a peptide amphiphile supramolecular polymer is designed to retain a function as a bioactive molecule or neurotrophic factor as provided by neurotrophic factor peptide sequences comprised in its peptide amphiphile subunits.

A neurotrophic factor peptide (or neurotrophic factor peptide sequence) refers to a peptide molecule with a neurotrophic or bioactive function and effects on cells, in particular regeneration, differentiation, stimulation, regrowth or repair of nervous tissues or cells.

Neuronal recovery activator (NRA) refers to a complex comprises the molecular elements of: an optional linker to a cognate ligand, an optional alkyl chain, an optional flexible peptide linker sequence, a linker peptide sequence, and a peptide sequence that functions as a neurotrophic factor or bioactive molecule. Examples for such neurotrophic factor peptide sequences are IKVAV or YRSRKYSSWYVALKR. Desirable neurotrophic effects of cellular activation and regeneration achieved by NRAs can be further enhanced by combining the use of one of more NRAs with additionally providing an aligned scaffold, or with a neurotrophic microenvironment, or a combination thereof. A NRA may comprise an optional alkyl chain located anywhere in the molecular structure of the NRA. The linkage length of such an alkyl chains may range from 1-2 carbon atoms, 2-4 carbon atoms, 4-6 carbon atoms, 6-8 carbon atoms, or 8-10 carbon atoms, and a combination thereof. Other examples of NRAs may comprise: brain derived growth factor (BDNF), ciliary neurotrophic factor (CNTF), neurotrophin-3 (NT-3), fibroblast growth factor2 (FGF-2), laminin signal peptide, collagen-binding neurotrophic factor 3, glial derived growth factor (GDNF), nerve growth factor (NGF), basic fibroblast growth factor (BFGF), stromal cell derived factor-1 alpha (SDF-1alpha), vascular endothelial growth factor (VEGF), hepatocyte growth factor (HGF), collagen-binding hepatocyte growth factor (cbHGF), ciliary neurotrophic factor (CNTF), basic fibroblast growth factor (bFGF), nerve growth factor precursor, proNGF, LIP1, LIP2, insulin-like growth factor (IGF), erythropoietin (EPO), brain derived neurotrophic factor (BDNF), granulocyte-colony stimulating factor (G-CSF), cerebral dopamine neurotrophic factor (CDNF), fibroblast growth factor (FGF), acidic fibroblast growth factor (aFGF), basic fibroblast growth factor (bFGF), epidermal growth factor (EGF), glial cell line-derived neurotrophic factor (GDNF) family ligand (GFL), heparin binding epidermal growth factor (HB-EGF), and a combination thereof.

A flexible peptide linker sequence refers to a variety of peptide sequences that are useful to increase the flexibility, molecular dynamics and water solubility of the NRA. Some preferred examples are AAGG, AAGG, VVAA, AAVV, GAGA, AGAG, AVAV, VAVA. The solubility of a peptide, of a peptide amphiphile and of an NRA is determined mainly by its overall polarity. Acidic peptides can be reconstituted in basic buffers, whereas basic peptides can be dissolved in acidic solutions. Hydrophobic peptides and neutral peptides that contain large numbers of hydrophobic or polar uncharged amino acids should be dissolved in small amounts of organic solvent such as DMSO, DMF, acetic acid, acetonitrile, methanol, propanol, or isopropanol, and then diluted using water. DMSO should not be used with peptides that methionine or free cysteine because it might oxidize the side-chain. It is useful to assign a value of −1 to each acidic residue (Asp [D], Glu [E], and the C-terminal —COOH). Assign a value of +1 to each basic residue (Arg [R], Lys [K], His [H], and the N-terminal —NH2). Then estimate the overall charge of the peptide. If the overall charge of the peptide is positive, the peptide is basic. If the peptide fails to dissolve in water, dissolve the peptide in a small amount of 10-25% acetic acid. If this fails, add TFA (10-50 μl) to solubilize the peptide, and then dilute to the desired concentration. If the overall charge of the peptide is negative, the peptide is acidic. Acidic peptides may be soluble in PBS (pH 7.4). If this fails, add a small amount of basic solvent such as 0.1 M ammonium bicarbonate to dissolve the peptide, then add water to the desired concentration. Peptides that contain free cysteines should be dissolved in de-gassed acidic buffers because thiol moieties will be oxidized rapidly to disulfides at pH>7. If the overall charge of the peptide is 0, the peptide is neutral. Neutral peptides usually dissolve in organic solvents. First, try to add a small amount of acetonitrile, methanol, or isopropanol. For very hydrophobic peptides, try to dissolve the peptide in a small amount of DMSO, and then dilute the solution with water to the desired concentration. For Cys-containing peptides, use DMF instead of DMSO. For peptides that tend to aggregate, add 6 M guanidine, HCl, or 8 M urea, and then proceed with the necessary dilutions. Positively charged residues: K, R, H, and the N-terminus Negatively charged residues: D, E, and the C-terminus. Hydrophobic uncharged residues: F, I, L, M, V, W, and Y. Uncharged residues: G, A, S, T, C, N, O, P, acetyl, and amide. Examples: RKDEFILGASRHD: (+5)+(−4)=+1, a basic peptide. EKDEFILGASEHR: (+4)+(−5)=−1, an acidic peptide. AKDEFILGASEHR: (+4)+(−4)=0, a neutral peptide.

A linker peptide sequence refers to a variety of peptide sequences that are used as linkers and to increase molecular separation (distance) from an optional attachment point or linker to a cognate ligand, which may be attached to the surface of a magnetic particle. Some preferred examples of linker peptide sequences are: EG, EEG, EEEG, EEEEG, EEEEEG, EEEEEEG, EEE, GG, GGE, GGGE, GGGGE, GGGGGE, or a combination thereof. Amino acids E and D carry a net negative charge, which can be useful to increase water solubility as described above. Amino acids R, K and H carry a net positive charge, which can be useful to increase water solubility as described above. Combinations of amino acids that have a net charge of about zero are not preferred due their decreased water solubility.

A neurotrophic factor peptide sequence preferably comprises the sequences IKVAV, also known as a laminin signal peptide, and YRSRKYSSWYVALKR, also known as a fibroblast growth factor2 (FGF-2) mimetic signal peptide.

A neurite or neuronal process refers to any projection from the cell body of a neuron and the projection can be an axon or a dendrite. The term neurite or neuronal process is frequently used when speaking of immature or developing neurons, especially of cells in culture, because it can be difficult to tell fully functional, i.e. electrical impulse conducting axons from dendrites before differentiation is complete.

Neuroregeneration and the regeneration of nervous tissue refer to the regrowth or repair of nervous tissues, cells or cell products. Such mechanisms may include generation of new neurons, glia, axons, neurites, myelin, or synapses. Neuroregeneration differs between the peripheral nervous system (PNS) and the central nervous system (CNS) by the functional mechanisms and especially the extent and speed. When an axon is damaged, the distal segment undergoes Wallerian degeneration, losing its myelin sheath. The proximal segment can either die by apoptosis or undergo the chromatolytic reaction, which is an attempt at repair. In the CNS, synaptic stripping occurs as glial foot processes invade the dead synapse. Macrophages and Schwann cells (in the PNS) can release neurotrophic factors that enhance regrowth.

Inhibitory influences of the glial and extracellular environment in the CNS refers to processes which suppress spontaneous recovery of the CNS from CNS injury. The hostile, non permissive growth environment is, in part, created by the migration of myelin associated inhibitors, astrocytes, oligodendrocytes, oligodendrocyte precursors, and microglia. The environment within the CNS, especially following trauma, counteracts the repair of myelin and neurons. Growth factors are not expressed or re-expressed; for instance, the extracellular matrix is lacking laminins. Glial scars rapidly form, and the glia actually produce factors that inhibit remyelination and axon repair; for instance, NOGO and NI 35. The axons themselves also lose the potential for growth with age, due to a decrease in GAP 43 expression. These factors contribute to the formation of what is known as a glial scar, which axons cannot grow across. The proximal segment attempts to regenerate after injury, but its growth is hindered by the lack of a favorable neurotrophic microenvironment. Central nervous system axons (as in the spinal cord) can regrow in permissive environments. Thus, one of the major problems to central nervous system axonal regeneration is suppressing or eliminating inhibitory physical obstacles and other factors that begin to form at the lesion site soon after injury and prevent the crossing of neurons across the lesion.

Glial scar formation refers to processes induced following damage to the nervous system. In the central nervous system, glial scar formation inhibits nerve regeneration, which leads to a loss of function. Several families of bioactive molecules are released that promote and drive glial scar formation. For instance, transforming growth factors B 1 and 2, interleukins, and cytokines play a role in the initiation of scar formation. The accumulation of reactive astrocytes at the site of injury and the upregulation of molecules that are inhibitory for neurite outgrowth contribute to the failure of neuroregeneration. The upregulated molecules alter the composition of the extracellular matrix in a way that has been shown to inhibit neurite outgrowth extension. This scar formation involves several cell types and families of molecules.

Chondroitin sulfate proteoglycan refers to a group of molecules involved in glial scar formation. In response to scar inducing factors, like those discussed above, astrocytes upregulate the production of chondroitin sulfate proteoglycans (CSPGs). Astrocytes are a predominant type of glial cell in the central nervous system that provide many functions including damage mitigation, repair, and glial scar formation. CSPGs inhibit neurite outgrowth and regeneration in vitro and in vivo.

Oligodendrocyte precursor cells refer to another type of glial cell found in the central nervous system that play a role in glial scar formation. These cell types can develop into a normal oligodendrocyte or a glial fibrillary acidic protein positive astrocyte depending on environmental factors. NG2 is found on the surface of these cells and has been shown to inhibit neurite outgrowth extension, as well. These are high molecular weight transmembrane molecules with the largest portion extending into the extracellular space. Following injury to the central nervous system, NG2 expressing oligodendrocyte precursor cells are seen around the site of injury within 48 hours of the initial injury. The number of NG2 expressing cells continues to increase for the next three to five days and high levels of NG2 are seen within seven ten days of the injury. NG2 inhibits neurite growth inhibition.

Oligodendrocyte refers to a neuroglial cell similar to an astrocyte but with fewer protuberances, concerned with the production of myelin in the central nervous system equivalent to the function performed by Schwann cells in the peripheral nervous system.

Keratan sulfate proteoglycans refer to molecules which are like the chondroitin sulfate proteoglycans, in that keratan sulfate proteoglycan (KSPG) production is upregulated in reactive astrocytes during glial scar formation. KSPGs have also been shown to inhibit neurite outgrowth extension, limiting nerve regeneration. Inhibitory proteins in oligodendritic or glial debris include the following seven proteins: (1) NOGO, an inhibitor of remyelination in the CNS; (2) NI 35, a non permissive growth factor from myelin; (3) MAG, a Myelin associated glycoprotein; (4) Oligodendrocyte Myelin glycoprotein; (5) Ephrin B3, which inhibits remyelination; (6) Semaphorin 4D, which inhibits remyelination; and (7) Semaphorin 3A, present in the scar which forms in both central nervous system and peripheral nerve injuries, which contributes to the outgrowth inhibitory properties of these scars.

Autologous nerve grafting refers to a nerve autograft used to repair large lesion gaps in the peripheral nervous system and proposed for some treatments of CNS damage, such as in SCI. Nerve (or spinal cord) segments are taken from another part of the body (the donor site) and inserted into the lesion to provide endoneurial tubes for axonal regeneration across the gap. Often the final outcome in PNS repair is only limited function recovery. Partial deinnervation is experienced at the donor site, and multiple surgeries are often required to harvest nerve tissue for additional nerve implant surgery. A nearby donor site may be used to supply innervation to lesioned nerves. Trauma to the donor site can be minimized by utilizing a technique known as end to side repair. In this procedure, an epineurial window is created in the donor nerve and the proximal stump of the lesioned nerve is sutured over the window. Regenerating axons are redirected into the stump. The efficacy of this technique is dependent upon the degree of neurectomy. The more neurectomy the greater possibility for axon regeneration within the lesioned nerve, but with the consequence of increasing nerve deficit to the donor. Some evidence suggests that local delivery of soluble neurotrophic factors at the site of autologous nerve grafting may enhance axon regeneration within the graft and help expedite functional recovery of a paralyzed target.

Nerve guidance conduit refers to the development of artificial nerve guidance conduits in order to guide axonal regrowth. The creation of artificial nerve conduits is also known as entubulation because the nerve ends and intervening gap are enclosed within a tube composed of biological or synthetic materials. Channels and other forms of guidance structures, other than fibers, can also be utilized.

Spinal cord functional recovery refers to a possible regaining of function that was lost after SCI. There currently is no cure for spinal cord injury, although significant progress has been made in even getting patients to walk again through the use of implantable devices that provide external stimulation of severed nerves (Greiner, 2021). One challenge in achieving functional recovery is to develop approaches that encourage directional axonal regeneration that extends through the lesion cavity and reconnects the two severed ends of the spinal cord.

Fibrotic glial scar: A key problem in spinal cord injury is that within about two weeks scar tissue has formed in the damaged area of the spine that largely prevents subsequent growth and connection of nerve cells that would be required to restore electrical conduction and functionality in the spine. Glial scar formation (gliosis) is understood to be a reactive cellular process involving astrogliosis that occurs after injury to the central nervous system. As with scarring in other organs and tissues, the glial scar is the body's evolutionary mechanism to try and protect itself after injury and begin the healing process in the nervous system.

Astrogliosis and astrocytosis refer to an abnormal increase in the number of astrocytes due to the destruction of nearby neurons from CNS trauma, infection, ischemia, stroke, autoimmune responses, and neurodegenerative disease. Typically it occurs over the course of several days following the injury as part of the body's normal healing mechanism. Unfortunately however this natural process ends up being counterproductive to regaining nerve function because it leads to the formation of scar-like layers that interfere with the ability of still functioning as well as newly formed neurons and neurites to reconnect the damaged or severed nerve fiber ends. One embodiment of the present invention is conceived to include removing the increased layer of astrocytes and other cells to expose a 'fresh' layer of neurons to enhance regeneration by a formulation of the present invention treating neural tissue damage.

Astrocyte refers to a star shaped glial cell of the central nervous system that is related to microglia, which are glial cells derived from mesoderm that function as macrophages (scavengers) in the central nervous system and form part of the reticuloendothelial system. Astrocyte proportion varies by region and ranges from 20% to 40% of all glia. Astrocytes perform many supportive functions, including biochemical support of endothelial cells that form the blood brain barrier, provision of nutrients to the nervous tissue, maintenance of extracellular ion balance, and a role in the repair and scarring process of the brain and spinal cord following traumatic injuries. Astrocytes propagate intercellular Ca2+ waves over long distances in response to stimulation, and, similar to neurons, release transmitters (called gliotransmitters) in a Ca2+ dependent manner. Astrocytes also signal to neurons through Ca2+ dependent release of glutamate.

In one aspect, disclosed is a method of regenerating a nerve fiber in a damaged neural tissue of a patient, the method comprising the steps of: administering an aqueous formulation comprising magnetic particles, a bioactive molecule and a neurotrophic microenvironment to the damaged neural tissue in the patient; applying a magnetic field in an orientation which is parallel to the nerve fiber; using the magnetic field for aligning the magnetic particles; forming one or more aligned chains of the magnetic particles in the magnetic field as a scaffold to guide directional growth of regenerating nerve cells; and reconnecting damaged nerve ends in the damaged neural tissue of the patient.

The method further comprising an earlier step of functionalizing surfaces of the magnetic particles with one or more bioactive molecules prior to administering the aqueous formulation comprising the magnetic particles to the damaged neural tissue in the patient, wherein the surfaces of the magnetic particles are functionalized with the one or more bioactive molecules selected from the group consisting of: a neurotrophic factor peptide, a neuronal recovery activator, a neurotrophic molecule, a neurobiological molecule, a peptide amphiphile, a peptide amphiphile supramolecular polymer, and a combination thereof. The neuronal recovery activator comprises a molecule selected from the group consisting of the peptide sequences IKVAV, YRSRKYSSWYVALKR, and a combination thereof.

The neuronal recovery activator comprises a peptide comprised in a molecule selected from the group consisting of brain derived growth factor (BDNF), ciliary neurotrophic factor (CNTF), neurotrophin-3 (NT-3), fibroblast growth factor2 (FGF-2), laminin signal peptide, collagen-binding neurotrophic factor 3, glial derived growth factor (GDNF), nerve growth factor (NGF), basic fibroblast growth factor (BFGF), stromal cell derived factor-1 alpha (SDF-1alpha), vascular endothelial growth factor (VEGF), hepatocyte growth factor (HGF), collagen-binding hepatocyte growth factor (cbHGF), ciliary neurotrophic factor (CNTF), basic fibroblast growth factor (bFGF), nerve growth factor precursor, proNGF, LIP1, LIP2, insulin-like growth factor (IGF), erythropoietin (EPO), brain derived neurotrophic factor (BDNF), granulocyte-colony stimulating factor (G-CSF), cerebral dopamine neurotrophic factor (CDNF), fibroblast growth factor (FGF), acidic fibroblast growth factor (aFGF), basic fibroblast growth factor (bFGF), epidermal growth factor (EGF), glial cell line-derived neurotrophic factor (GDNF) family ligand (GFL), heparin binding epidermal growth factor (HB-EGF), and a combination thereof.

The neuronal recovery activator comprises an antibody selected from the group consisting of antibodies against NOGO, NI-35, a myelin-associated glycoprotein (MAG), oligodendrocyte myelin glycoprotein, ephrin B3, semaphorin 4D, semaphorin 3A, and a combination thereof.

The neurotrophic microenvironment comprises a substance selected from the group consisting of a decellularized porcine spinal cord, a decellularized porcine urinary bladder, a decellularized porcine omentum, a hyaluronic acid-based hydrogel, a Poly-ε-caprolacton (PCL) hydrogel, a self-assembling peptide-based hydrogel, a RADA16-I hydrogel, a RADA16-PRG self-assembled nanopeptide scaffold (SAPNS), a PCL/PEG/FGF2/EGF/GDNF "five-in-one" composite scaffold, a hydroxyl ethyl methacrylate [2-(methacryloyloxy)ethyl] trimethylammonium chloride (HEMA-MOETACL) hydrogel, a poly(E-caprolactone-co-ethyl ethylene phosphate) nanofiber hydrogel, a heparin-poloxamer (HP) hydrogel, a poly (lactic-co-glycolic acid) (PLGA), a thermosensitive quaternary ammonium chloride chitosan/β-glycerophosphate (HACC/β-GP) hydrogel, a fibrous porous silk scaffold (FPSS), a gelatin-furfurylamine hydrogel, a sodium hyaluronate-CNTF (ciliary neurotrophic factor) scaffold, a 2-oxa-spiro [5.4]decane-based scaffold, a poly(2-hydroxyethyl methacrylate) (PHEMA), poly(lactic-co-glycolic acid) (PLGA), poly(e-caprolactone fumarate), alginate (Alg) microspheres on silk fibroin (SF) scaffold (SF/Alg composites scaffold), polyethylene glycol (PEG) cross-linked poly(N-isopropylacrylamide) (PNIPAAm), collagen-IV, fibronectin, laminin, a taxol-containing liposome, a cerebral dopamine neurotrophic factor (CDNF)-containing liposome, and a combination thereof.

The aqueous formulation comprising the magnetic particles, the bioactive molecules and the neurotrophic microenvironment further comprises a molecule selected from the group consisting of a neuronal recovery activator, a neurotrophic molecule, a neuronal cell growth factor, a chemotactic factor, a cell proliferation factor, a directional cell growth factor, a neuronal regeneration signaling molecule, a laminin, an inhibitor of glial cell induced scar formation, an inhibitor of astrocyte cell induced scar formation, an inhibitor of oligodendrocyte cell induced scar formation, an inhibitor of astrocyte precursor cell induced scar formation, an inhibitor of oligodendrocyte precursor cell induced scar formation, an inhibitor of 4 sulfation on astrocyte derived chondroitin sulfate proteoglycan, an inhibitor of chondroitin sulfate proteoglycan phosphacan, an inhibitor of 15 chondroitin sulfate proteoglycan neurocan, a chondroitinase ABC, an inhibitor of chondroitin sulfate proteoglycan 4, an inhibitor of neuron glial antigen 2, an antibody to chondroitin sulfate proteoglycan 4, an antibody against neuron glial antigen 2, an inhibitor of glial cell expression of chondroitin sulfate proteoglycan 4, an inhibitor of glial cell expression of neuron glial antigen 2, an inhibitor of keratan sulfate synthesis, an inhibitor of glial cell expression of an enzyme involved in keratin sulfate synthesis, an inhibitor of an oligodendritic cell debris origin neuroregeneration inhibiting protein, an inhibitor of a glial cell debris origin neuroregeneration inhibiting protein, an antibody against myelination inhibitory factor NI 35, an antibody against myelination inhibitory factor NOGO, an anti-oxidants, cerium oxide particles, an amino acid, a phospholipid, a lipid, a vitamin, an anticoagulant, and a combination thereof.

The method further comprising the step of stabilizing the aligned chains of the magnetic particles in the magnetic field using a crosslinking polymer architecture for locking the aligned chains of the magnetic particles into place after the step in claim 1 of using the magnetic field for aligning the magnetic particles and forming the one or more aligned chains of the magnetic particles in the magnetic field as the scaffold to guide directional growth of regenerating nerve cells.

The crosslinking polymer architecture for stabilizing the aligned chains of the magnetic particles is formed using molecules selected from the group consisting of psoralen, methyl methacrylate, avidin, streptavidin, antibodies, antigens, ligands, biotin, fluorescein, laminin, peptide amphiphile supramolecular polymers, DNA hybridization molecules, DNA origami, DNA dendrimers, aptamers, protein-protein binding, protein DNA binding, metal ion chelators, magnetic elements, magnetic compounds, magnetic crystals, His tags, polyethylene glycol linkers, agarose, acrylamide, collagen, phase transfer catalysts, and any combination thereof.

The method further comprising the step of applying a magnetic field gradient which is parallel to the nerve fiber orientation so as to laterally move the magnetic particles and the aligned fibers towards severed nerve endings through the use of the magnetic field gradient, thereby inducing the magnetic particles and the aligned fibers to enter available spaces between existing axons, neurons and other cells of the injured cord, thereby enhancing contact or forming connections between the aligned fibers and existing axons or neurons.

The method further comprising the step of removing the magnetic field and magnetic field gradient which is parallel to the nerve fiber orientation after the step of stabilizing the aligned chains of the magnetic particles using the cross-linking polymer architecture.

In a preferred implementation, the magnetic field has a strength between about 1 milli Tesla to about 12 Tesla.

TABLE 1

| peptide sequences | |
|---|---|
| Sequence ID | Sequence |
| Seq. ID. 1 | YRSRKYSSWYVALKR |
| Seq. ID. 2 | IKVAV |

TABLE 1-continued

| peptide sequences | |
|---|---|
| Sequence ID | Sequence |
| Seq. ID. 3 | EEEG |
| Seq. ID. 4 | AAGG |
| Seq. ID. 5 | VVAA |
| Seq. ID. 6 | AAVV |
| Seq. ID. 7 | GAGA |
| Seq. ID. 8 | AGAG |
| Seq. ID. 9 | AVAV |
| Seq. ID. 10 | VAVA |
| Seq. ID. 11 | EEEEG |
| Seq. ID. 12 | EEEEEG |
| Seq. ID. 13 | EEEEEEG |
| Seq. ID. 14 | GGGE |
| Seq. ID. 15 | GGGGE |
| Seq. ID. 16 | GGGGGE |

SEQUENCE LISTING

```
Sequence total quantity: 16
SEQ ID NO: 1            moltype = AA  length = 15
FEATURE                 Location/Qualifiers
source                  1..15
                        mol_type = protein
                        organism = synthetic construct
SEQUENCE: 1
YRSRKYSSWY VALKR                                                15

SEQ ID NO: 2            moltype = AA  length = 5
FEATURE                 Location/Qualifiers
source                  1..5
                        mol_type = protein
                        organism = synthetic construct
SEQUENCE: 2
IKVAV                                                           5

SEQ ID NO: 3            moltype = AA  length = 4
FEATURE                 Location/Qualifiers
source                  1..4
                        mol_type = protein
                        organism = synthetic construct
SEQUENCE: 3
EEEG                                                            4

SEQ ID NO: 4            moltype = AA  length = 4
FEATURE                 Location/Qualifiers
source                  1..4
                        mol_type = protein
                        organism = synthetic construct
SEQUENCE: 4
AAGG                                                            4

SEQ ID NO: 5            moltype = AA  length = 4
FEATURE                 Location/Qualifiers
source                  1..4
                        mol_type = protein
                        organism = synthetic construct
```

```
SEQUENCE: 5
VVAA                                                                    4

SEQ ID NO: 6             moltype = AA  length = 4
FEATURE                  Location/Qualifiers
source                   1..4
                         mol_type = protein
                         organism = synthetic construct
SEQUENCE: 6
AAVV                                                                    4

SEQ ID NO: 7             moltype = AA  length = 4
FEATURE                  Location/Qualifiers
source                   1..4
                         mol_type = protein
                         organism = synthetic construct
SEQUENCE: 7
GAGA                                                                    4

SEQ ID NO: 8             moltype = AA  length = 4
FEATURE                  Location/Qualifiers
source                   1..4
                         mol_type = protein
                         organism = synthetic construct
SEQUENCE: 8
AGAG                                                                    4

SEQ ID NO: 9             moltype = AA  length = 4
FEATURE                  Location/Qualifiers
source                   1..4
                         mol_type = protein
                         organism = synthetic construct
SEQUENCE: 9
AVAV                                                                    4

SEQ ID NO: 10            moltype = AA  length = 4
FEATURE                  Location/Qualifiers
source                   1..4
                         mol_type = protein
                         organism = synthetic construct
SEQUENCE: 10
VAVA                                                                    4

SEQ ID NO: 11            moltype = AA  length = 5
FEATURE                  Location/Qualifiers
source                   1..5
                         mol_type = protein
                         organism = synthetic construct
SEQUENCE: 11
EEEEG                                                                   5

SEQ ID NO: 12            moltype = AA  length = 6
FEATURE                  Location/Qualifiers
source                   1..6
                         mol_type = protein
                         organism = synthetic construct
SEQUENCE: 12
EEEEEG                                                                  6

SEQ ID NO: 13            moltype = AA  length = 7
FEATURE                  Location/Qualifiers
source                   1..7
                         mol_type = protein
                         organism = synthetic construct
SEQUENCE: 13
EEEEEEG                                                                 7

SEQ ID NO: 14            moltype = AA  length = 4
FEATURE                  Location/Qualifiers
source                   1..4
                         mol_type = protein
                         organism = synthetic construct
SEQUENCE: 14
GGGE                                                                    4

SEQ ID NO: 15            moltype = AA  length = 5
FEATURE                  Location/Qualifiers
source                   1..5
                         mol_type = protein
```

-continued

```
                        organism = synthetic construct
SEQUENCE: 15
GGGGE                                                                 5

SEQ ID NO: 16           moltype = AA  length = 6
FEATURE                 Location/Qualifiers
source                  1..6
                        mol_type = protein
                        organism = synthetic construct
SEQUENCE: 16
GGGGGE                                                                6
```

What is claimed is:

1. A method of promoting magnetically guided axon regeneration in a desired direction across an injury site in damaged neural tissue so as to reconnect nerve ends of a severed nerve and restore nerve conduction, the method comprising:

administering into the injury site a liquid formulation comprising magnetic particles;

applying an external magnetic field having homogeneous magnetic field lines within the injury site to force magnetic moments of the magnetic particles to align and thereby amplify attractions between the magnetic particles so as to adhere together and aggregate in situ into self-assembled, longitudinally aligned parallel chains within the injury site;

wherein the magnetic particles are functionalized with one or more neuronal recovery activators, each neuronal recovery activator comprising at least one bioactive molecule selected from the group consisting of:

(i) laminin, (ii) a laminin-derived peptide sequence, (iii) a fibroblast growth factor (FGF) mimetic peptide sequence, (iv) glial cell-derived neurotrophic factor (GDNF), (v) chondroitinase ABC (ChABC), or (vi) any combination thereof;

wherein each neuronal recovery activator comprises a linker peptide sequence selected from the group consisting of AAGG: (SEQ ID NO: 4), VVAA (SEQ ID NO: 5), AAVV (SEQ ID NO: 6), GAGA (SEQ ID NO: 7), AGAG (SEQ ID NO: 8), AVAV (SEQ ID NO: 9), VAVA (SEQ ID NO: 10), EG, EEG, EEEG (SEQ ID NO: 3), EEEEG (SEQ ID NO: 11), EEEEEG (SEQ ID NO: 12), EEEEEEG (SEQ ID NO: 13), EEE, EEEE, GG, GGE, GGGE (SEQ ID NO: 14), GGGGE (SEQ ID NO: 15), GGGGGE (SEQ ID NO: 16), and combinations thereof;

wherein: (i) the laminin-derived peptide sequence is IKVAV, (ii) the fibroblast growth factor mimetic peptide sequence is YRSRKYSSWYVALKR, or (iii) both (i) and (ii).

2. The method according to claim 1, wherein the one or more neuronal recovery activators comprise a biotin linker and a cognate ligand on the functionalized magnetic particles is streptavidin, neutravidin, or any combination thereof.

3. The method according to claim 1, wherein at least one of the neuronal recovery activators comprises a peptide amphiphile supramolecular polymer and contains an alkyl chain.

4. The method according to claim 1, wherein the liquid formulation further comprises an antibody selected from the group consisting of: antibodies against NOGO, NI-35, a myelin-associated glycoprotein (MAG), oligodendrocyte myelin glycoprotein, ephrin B3, semaphorin 4D, semaphorin 3A, and combinations thereof.

5. The method according to claim 1, wherein the liquid formulation further comprises a hydrogel matrix forming compound, and wherein after a period of time the liquid formulation administered into the injury site solidifies to lock in position the parallel chains of the magnetic particles.

6. The method of claim 5, wherein the hydrogel matrix forming compound is selected from the group consisting of: a fibrin with thrombin hydrogel, a collagen hydrogel, a peptide modified polyethylene glycol hydrogel, agarose, methylcellulose, methyl methacrylate, hyaluronan, polyethylene oxide, polyvinyl-pyrrolidone, poly(2-acrylamido-2-methyl-1-propanesulfonic acid), and combinations thereof.

7. The method according to claim 1, wherein the liquid formulation further comprises cells selected from the group consisting of: embedded cells, stem cells, neural stem cells, neural progenitor cells, induced pluripotent stem cells, induced pluripotent stem cell-derived neurons, neurons, Schwann cells, and combinations thereof.

8. The method according to claim 1, wherein the liquid formulation further comprises a molecule selected from the group consisting of: a neuronal cell growth factor, a chemotactic factor, a cell proliferation factor, a directional cell growth factor, a neuronal regeneration signaling molecule, a laminin, an inhibitor of glial cell induced scar formation, an inhibitor of astrocyte cell induced scar formation, an inhibitor of oligodendrocyte cell induced scar formation, an inhibitor of astrocyte precursor cell induced scar formation, an inhibitor of oligodendrocyte precursor cell induced scar formation, an inhibitor of 4 sulfation on astrocyte derived chondroitin sulfate proteoglycan, an inhibitor of chondroitin sulfate proteoglycan phosphacan, an inhibitor of chondroitin sulfate proteoglycan neurocan, a chondroitinase ABC, an inhibitor of chondroitin sulfate proteoglycan 4, an inhibitor of neuron glial antigen 2, an antibody to chondroitin sulfate proteoglycan 4, an antibody against neuron glial antigen 2, an inhibitor of glial cell expression of chondroitin sulfate proteoglycan 4, an inhibitor of glial cell expression of neuron glial antigen 2, an inhibitor of keratan sulfate synthesis, an inhibitor of glial cell expression of an enzyme involved in keratin sulfate synthesis, an inhibitor of an oligodendritic cell debris origin neuroregeneration inhibiting protein, an inhibitor of a glial cell debris origin neuroregeneration inhibiting protein, an antibody against myelination inhibitory factor NI 35, an antibody against myelination inhibitory factor NOGO, an anti oxidants, cerium oxide particles, an amino acid, a phospholipid, a lipid, a vitamin, an anticoagulant, and combinations thereof.

9. The method according to claim 8, wherein in the nerve growth factor is a molecule selected from the group consisting of: neurotrophin-3 (NT-3), fibroblast growth factor2

(FGF-2), laminin signal peptide, collagen-binding neurotrophic factor 3, glial derived growth factor (GDNF), nerve growth factor (NGF), basic fibroblast growth factor (BFGF), stromal cell derived factor-1 alpha (SDF-1alpha), vascular endothelial growth factor (VEGF), hepatocyte growth factor (HGF), collagen-binding hepatocyte growth factor (cbHGF), ciliary neurotrophic factor (CNTF), basic fibroblast growth factor (bFGF), nerve growth factor precursor, proNGF, LIP1, LIP2, insulin-like growth factor (IGF), erythropoietin (EPO), brain derived neurotrophic factor (BDNF), granulocyte-colony stimulating factor (G-CSF), cerebral dopamine neurotrophic factor (CDNF), fibroblast growth factor (FGF), acidic fibroblast growth factor (aFGF), basic fibroblast growth factor (bFGF), epidermal growth factor (EGF), glial cell line-derived neurotrophic factor family ligand (GFL), heparin binding epidermal growth factor (HB-EGF), and combinations thereof.

10. The method according to claim 1, wherein the homogeneous magnetic field lines are oriented parallel to a longitudinal axis of a nerve fiber adjacent to the injury site such that the self-assembled chains guide axon regeneration along the longitudinal axis of the nerve fiber.

11. The method according to claim 1, wherein the magnetic particles are selected from superparamagnetic particles, ferromagnetic particles, ferrimagnetic particles, or combinations thereof.

12. The method according to claim 1, wherein the magnetic particles in the liquid formulation are randomly distributed when being administered.

13. The method according to claim 1, wherein the magnetic particles in the liquid formulation are randomly distributed when being administered and wherein the in situ aligning chains are stabilized by a crosslinking polymer architecture after having been administered into the injury site.

14. The method according to claim 1, wherein the aligned parallel chains are stabilized by a crosslinking polymer architecture after removal of the magnetic field using molecules selected from the group consisting of: avidin, streptavidin, neutravidin, biotin, laminin, biotinylated DNA, DNA hybridization molecules, and combinations thereof.

15. The method according to claim 1, further comprising using a crosslinking polymer architecture for stabilizing the parallel chains of the magnetic particles in the injury site, wherein the cross linking polymer architecture is selected from the group consisting of: a cross linking homopolymer of surface functionalized magnetic particles, a cross linking copolymer of different surface functionalized magnetic particles, a cross linking junction controlled branched polymer of the surface functionalized particles, and combinations thereof, and wherein the cross linking polymer architecture is formed using molecules selected from the group consisting of: psoralen, methyl methacrylate, avidin, streptavidin, biotin, antibodies against NOGO, a myelin-associated glycoprotein Nl-35, oligodendrocyte myelin glycoprotein, ephrin B3, semaphorin 4D, semaphorin 3, laminin, fluorescein, a DNA hybridization molecule, a DNA origami, a DNA dendrimer, an antigen, an aptamer, a protein binding DNA, a metal ion chelator, a His tag, a polyethylene glycol linker, an agarose, an acrylamide, a collagen, a phase transfer catalyst, and combinations thereof.

16. The method according to claim 1, wherein the liquid formulation further comprises a carrier selected from the group consisting of: a microsphere, a porous particle, a hydrogel, a decellularized extracellular matrix (ECM), a decellularized spinal cord, a decellularized omentum, a decellularized urinary bladder, a multiphase solution, a colloid, a capsule, a microcapsule, a liposome, isotonic saline, cerebrospinal fluid, spinal fluid, and combinations thereof.

17. The method according to claim 1, wherein the external magnetic field has a strength between about 0.0005 Tesla and about 10 Tesla, and wherein the magnetic field is produced using an electromagnet, a permanent magnet, or the electromagnet and the permanent magnet.

18. The method according to claim 1, wherein a magnetic field gradient is applied after the formation of aligned parallel chains, and wherein the magnetic field gradient is between 0.0001 Tesla/m to about 2 Tesla/m.

* * * * *